United States Patent
Carney et al.

(10) Patent No.: US 10,220,078 B2
(45) Date of Patent: Mar. 5, 2019

(54) METHODS OF USING THROMBIN DERIVATIVES TO TREAT MEDULLOBLASTOMA

(71) Applicants: Darrell Carney, Dickinson, TX (US); Carla Kantara, Dickinson, TX (US); Stephanie Moya, Dickinson, TX (US)

(72) Inventors: Darrell Carney, Dickinson, TX (US); Carla Kantara, Dickinson, TX (US); Stephanie Moya, Dickinson, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 213 days.

(21) Appl. No.: 14/736,735

(22) Filed: Jun. 11, 2015

(65) Prior Publication Data
US 2015/0359855 A1 Dec. 17, 2015

Related U.S. Application Data

(60) Provisional application No. 62/010,553, filed on Jun. 11, 2014.

(51) Int. Cl.
*A61K 38/48* (2006.01)
*A61K 41/00* (2006.01)

(52) U.S. Cl.
CPC ...... *A61K 38/4833* (2013.01); *A61K 41/0038* (2013.01); *C12Y 304/21005* (2013.01)

(58) Field of Classification Search
None
See application file for complete search history.

(56) References Cited

U.S. PATENT DOCUMENTS

| | | | |
|---|---|---|---|
| 5,352,664 A * | 10/1994 | Carney | C12Y 304/21005 424/94.64 |
| 5,500,412 A * | 3/1996 | Carney | C12Y 304/21005 514/21.4 |
| 6,627,731 B1 | 9/2003 | Carney et al. | |
| 6,630,572 B1 | 10/2003 | Carney et al. | |
| 6,815,416 B2 | 11/2004 | Carney et al. | |
| 6,855,687 B2 | 2/2005 | Carney et al. | |
| 6,861,407 B2 | 3/2005 | Carney | |
| 6,867,190 B2 | 3/2005 | Carney | |
| 6,894,027 B2 | 5/2005 | Carney et al. | |
| 6,914,050 B2 | 7/2005 | Carney et al. | |
| 7,034,001 B2 | 4/2006 | Carney | |
| 7,049,294 B2 | 5/2006 | Carney | |
| 7,214,661 B2 | 5/2007 | Carney | |
| 7,291,596 B2 | 11/2007 | Hobson et al. | |
| 7,304,035 B2 | 12/2007 | Carney et al. | |
| 7,378,500 B2 | 5/2008 | Carney | |
| 7,456,250 B2 | 11/2008 | Carney | |
| 7,713,934 B2 | 5/2010 | Carney | |
| 7,732,411 B2 | 6/2010 | Carney | |
| 7,833,982 B2 | 11/2010 | Carney | |
| 7,875,588 B2 | 1/2011 | Hobson et al. | |
| 7,919,457 B2 | 4/2011 | Carney | |
| 7,935,341 B2 | 5/2011 | Carney et al. | |
| 8,334,259 B2 | 12/2012 | Carney et al. | |
| 8,952,129 B2 | 2/2015 | Carney et al. | |
| 2005/0153893 A1 | 7/2005 | Carney | |
| 2005/0158301 A1 | 7/2005 | Carney | |
| 2010/0303793 A1 | 12/2010 | Olszewska-Pazdrak et al. | |
| 2010/0330028 A1 | 12/2010 | Olszewska-Pazdrak et al. | |
| 2011/0105400 A1 | 5/2011 | Steer et al. | |
| 2011/0110920 A1 | 5/2011 | Carney et al. | |
| 2011/0117075 A1 | 5/2011 | Carney et al. | |
| 2011/0319340 A1* | 12/2011 | Carney | A61K 38/4833 514/19.8 |
| 2013/0101574 A1 | 4/2013 | Carney | |
| 2015/0359855 A1 | 12/2015 | Carney et al. | |

FOREIGN PATENT DOCUMENTS

WO WO 2003/061689 A1 7/2003

OTHER PUBLICATIONS

Katz et al., Int. J. Radiation Oncology Biol. Phys. 2009, 73(4), 988-996.*
Gerber et al., Cancer Treatment Reviews, 2014, 40, 356-365.*
Ma et al. (Biophys J. Aug. 2005; 89(2): 1183-1193).*
Zawaski et al. ("The radioprotectant effect of a thrombin peptide (TP508, Chrysalin) on radiation-induced normal tissue toxicity in the brain" Poster PS6-47; 59th Annual Meeting of the Radiation Research Society; Sep. 14-18, 2013).*
Palmer ("Neurodevelopmental impacts on children treated for medulloblastoma: A review and proposed conceptual model" Dev Disabil Res Rev. 2008 ; 14(3): 203-210).*

(Continued)

*Primary Examiner* — Jennifer Pitrak McDonald
*Assistant Examiner* — Tara L Martinez
(74) *Attorney, Agent, or Firm* — Mueting, Raasch & Gebhardt, P.A.

(57) ABSTRACT

Provided herein are methods for using a thrombin peptide derivative to treat a medulloblastoma. In one embodiment, the method includes administering to a subject having a medulloblastoma an effective amount of a thrombin peptide derivative, and exposing cells of the medulloblastoma of the subject to a cancer treatment after administering the thrombin peptide derivative to the subject. An example of a cancer treatment is radiation therapy. In one embodiment, viability of cells of the medulloblastoma is decreased compared to viability of cells of the medulloblastoma before the administering and the exposing. The cells of the medulloblastoma having decreased viability can be cancer stem cells. In one embodiment, shrinkage of the medulloblastoma in the subject is increased compared to shrinkage of the medulloblastoma before the administering and the exposing.

41 Claims, 8 Drawing Sheets
Specification includes a Sequence Listing.

(56) References Cited

OTHER PUBLICATIONS

Adamski et al., "Advances in managing medulloblastoma and intracranial primitive neuro-ectodermal tumors," *F1000 Prime Reports*, Jul. 2014; 6:56.
American Type Culture Collection, "ATCC No. HTB-14," organism: *Homo sapiens*, human [online]; Manassas, VA. Retrieved on Jul. 20, 2016. Retrieved from the Internet:<URL:https://www.atcc.org/~/ps/HTB-14.ashx>; 3 pgs.
American Type Culture Collection, "ATCC No. HTB-186," organism: *Homo sapiens*, human [online]; Manassas, VA. Retrieved on Jul. 20, 2016. Retrieved from the Internet:<URL:http://www.atcc.org/~/ps/HTB-186.ashx>; 3 pgs.
Aparicio et al., "DNA double-strand break repair pathway choice and cancer," *DNA Repair*, Jul. 2014; 19:169-175.
Baker, *Controlled Release of Biologically Active Agents*, Wiley, New York, NY, 1987. Cover page, copyright page and table of contents; 5 pages.
Baryawno et al. Small-molecule inhibitors of phosphatidylinositol 3-kinase/Akt signaling inhibit Wnt/β-catenin pathway cross-talk and suppress medulloblastoma growth, *Cancer Research*, Jan. 2010; 70(1):266-276.
Blazek et al., Daoy medulloblastoma cells that express CD133 are radioresistant relative to CD133− cells, and the CD133+ sector is enlarged by hypoxia, *International Journal of Radiation Oncology -Biology -Physics*, Jan. 2007; 67(1):1-5.
Brun et al., "Survivin as a therapeutic target in Sonic hedgehog-driven medulloblastoma," *Oncogene*, Jul. 2015; 34(29):3770-3779.
"Cancer Facts & Figures 2015," American Cancer Society [retrieved on Jul. 19, 2016]. Retrieved from the Internet:<URL:http://www.cancer.org/acs/groups/content/@editorial/documents/document/acspc-044552.pdf>; 56 pages.
Cao et al., "Comparative study of the use of poly(glycolic acid), calcium alginate and pluronics in the engineering of autologous porcine cartilage," *J Biomater Sci Polym Ed.*, 1998; 9(5):475-487.
Carney et al., "Double-signal hypothesis for thrombin initiation of cell proliferation," *Semin Thromb Hemost.*, Jul. 1986; 12(3):231-240.
Castelo-Branco et al., "Promises and challenges of exhausting pediatric neural cancer stem cells," *Pediatric Research*, Apr. 2012; 71(4):523-528.
Chen et al., "Understanding and targeting cancer stem cells: therapeutic implications and challenges," *Acta Pharmacol Sin.* Jun. 2013; 34(6):732-740.
Fuchs, "Transcription factor NF-κB inhibitors as single therapeutic agents or in combination with classical chemotherapeutic agents for the treatment of hematologic malignancies," *Current Molecular Pharmacology*, 2010; 3:98-122.
Gajjar et al., "Medulloblastoma—translating discoveries from the bench to the bedside," *Nature Reviews Clinical Oncology*, 2014; 11:714-722.
Glenn et al., "Synthetic peptides bind to high-affinity thrombin receptors and modulate thrombin mitogenesis," *Pept Res.* Nov.-Dec. 1988; 1(2):65-73.
Greene et al., *Protective Groups in Organic Synthesis*, Third Edition, John Wiley & Sons, Inc., New York, NY, 1999. Cover page, copyright page, table of contents, and pp. 454-493.

Hoesel et al., "The complexity of NF-κB signaling in inflammation and cancer," *Molecular Cancer*, 2013; 12:86.
Hope et al., "Acute myeloid leukemia originates from a hierarchy of leukemic stem cell classes that differ in self-renewal capacity", *Nature Immunology*, 2004; 5:738-743.
Hu et al., "Targeting cancer stem cells: a new therapy to cure cancer patients," *Am J Cancer Res.*, 2012; 2(3):340-356.
Jung et al., "Cancer stem cell targeting: Are we there yet?" Archives of Pharmacal Research, Mar. 2015, 38(3):414-422.
Kantara et al., "Curcumin promotes autophagic survival of a subset of colon cancer stem cells, which are ablated by DCLK1-siRNA," *Cancer Research*, May 2014; 74(9):2487-2498.
Karin et al., "NF-κB in cancer: from innocent bystander to major culprit," *Nature Reviews Cancer*, Apr. 2002; 2:301-310.
Katz et al., "On the path to seeking novel radiosensitizers," *Int J Radiat Oncol Biol Phys.*, Mar. 2009; 73(4):988-996.
Krishnaswamy, "The transition of prothrombin to thrombin," *Journal of Thrombosis and Haemostasis*, 2013; 11(Suppl. 1):265-276.
Manoranjan et al., "Medulloblastoma stem cells: where development and cancer cross pathways," *Pediatric Research*, Apr. 2012; 71(4):516-522.
Matsuo et al., "Inhibitory potential of postnatal treatment with cyclopamine, a hedgehog signaling inhibitor, on medulloblastoma development in Ptch1 heterozygous mice," *Toxicologic Pathology*, 2014; 42:1174-1187.
Pal et al., "Chronic inflammation and cancer: potential chemoprevention through nuclear factor kappa B and p53 mutual antagonism," *Journal of Inflammation*, 2014; 11:23.
Parker et al., "Morphological, immunocytochemical and flow cytometric in vitro characterisation of a surface-adherent medulloblastoma," *Anticancer Research*, 2005; 25:3855-3864.
Polkinghorn et al., "Medulloblastoma: tumorigenesis, current clinical paradigm, and efforts to improve risk stratification," *Nature Clinical Practice Oncology*, May 2007; 4:295-304.
Raleigh et al., "Molecular targets and mechanisms of radiosensitization using DNA damage response pathways," *Future Oncology*, Feb. 2013; 9(2):219-233.
Raviraj et al., "Radiosensitizers, radioprotectors, and radiation mitigators," *Indian Journal of Dental Research*, 2014; 25(1):83-90.
Rycaj et al., "Cancer stem cells and radioresistance," *Int J Radiat Biol.*, Aug. 2014; 90(8):615-621.
Sharma et al., "Enhancement of chemotherapeutic efficacy by small molecule inhibition of NF-κB and checkpoint kinases," *Current Medicinal Chemistry*, Apr. 2007; 14(10):1061-1074.
Sims et al., "Injectable Cartilage Using Polyethylene Oxide Polymer Substrates," *Plastic & Reconstructive Surgery*, Oct. 1996; 98(5):843-850.
Spiller et al., "Inhibition of nuclear factor kappa-B signaling reduces growth in medulloblastoma in vivo," *BMC Cancer*, 2011; 11:136.
Taylor et al., "Molecular subgroups of medulloblastoma: the current consensus," *Acta Neuropathol.*, Apr. 2012; 123(4):465-472.
Whittier et al., "G-protein coupled receptor expression patterns delineate medulloblastoma subgroups," *Acta Neuropathologica Communications*, 2013; 1:66.
Zeltzer et al., "Metastasis stage, adjuvant treatment, and residual tumor are prognostic factors for medulloblastoma in children: conclusions from the Children's Cancer Group 921 randomized phase III study," *Journal of Clinical Oncology*, Mar. 1999; 17(3):832-845.

* cited by examiner

Fig. 2Bii.
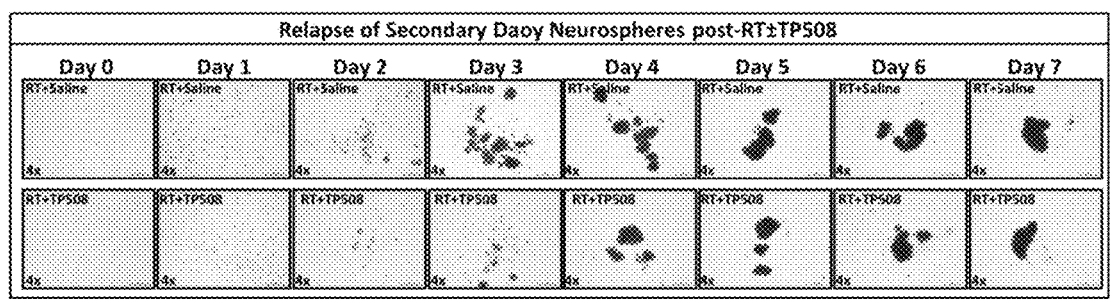
Fig. 2C.
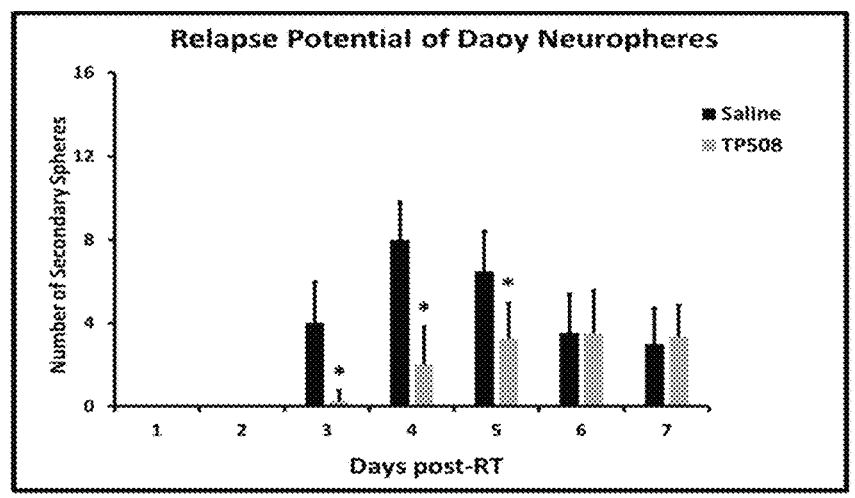

SEQUENCE LISTING

```
<160> NUMBER OF SEQ ID NOS: 30

<210> SEQ ID NO 1
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa at this position may be Glu or Gln
```

```
<220> FEATURE:
<221> NAME/KEY: MISC_FEATURE
<222> LOCATION: (13)..(13)
<223> OTHER INFORMATION: Xaa at this position may be Phe, Met, Leu, His
      or Val

<400> SEQUENCE: 1

Arg Gly Asp Ala Cys Xaa Gly Asp Ser Gly Gly Pro Xaa Val
1               5                   10

<210> SEQ ID NO 2
<211> LENGTH: 23
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (15)..(15)
<223> OTHER INFORMATION: Xaa at this position may be Glu or Gln
<220> FEATURE:
<221> NAME/KEY: MISC_FEATURE
<222> LOCATION: (22)..(22)
<223> OTHER INFORMATION: Xaa at this position may be Phe, Met, Leu, His
      or Val

<400> SEQUENCE: 2

Ala Gly Tyr Lys Pro Asp Glu Gly Lys Arg Gly Asp Ala Cys Xaa Gly
1               5                   10                  15

Asp Ser Gly Gly Pro Xaa Val
            20

<210> SEQ ID NO 3
<211> LENGTH: 23
<212> TYPE: PRT
<213> ORGANISM: Homo sapiens

<400> SEQUENCE: 3

Ala Gly Tyr Lys Pro Asp Glu Gly Lys Arg Gly Asp Ala Cys Glu Gly
1               5                   10                  15

Asp Ser Gly Gly Pro Phe Val
            20

<210> SEQ ID NO 4
<211> LENGTH: 14
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa at this position may be Glu or Gln
<220> FEATURE:
<221> NAME/KEY: MISC_FEATURE
<222> LOCATION: (13)..(13)
<223> OTHER INFORMATION: Xaa at this position may be Phe, Met, Leu, His
      or Val

<400> SEQUENCE: 4

Arg Gly Asp Ala Xaa Xaa Gly Asp Ser Gly Gly Pro Xaa Val
1               5                   10

<210> SEQ ID NO 5
<211> LENGTH: 23
```

```
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (14)..(14)
<223> OTHER INFORMATION: Xaa at this position may be alanine, glycine,
      serine or an S-protected cysteine
<220> FEATURE:
<221> NAME/KEY: MISC_FEATURE
<222> LOCATION: (15)..(15)
<223> OTHER INFORMATION: Xaa at this position may be Glu or Gln
<220> FEATURE:
<221> NAME/KEY: MISC_FEATURE
<222> LOCATION: (22)..(22)
<223> OTHER INFORMATION: Xaa at this position may be Phe, Met, Leu, His
      or Val

<400> SEQUENCE: 5

Ala Gly Tyr Lys Pro Asp Glu Gly Lys Arg Gly Asp Ala Xaa Xaa Gly
1               5                   10                  15

Asp Ser Gly Gly Pro Xaa Val
            20

<210> SEQ ID NO 6
<211> LENGTH: 23
<212> TYPE: PRT
<213> ORGANISM: Homo sapiens

<400> SEQUENCE: 6

Ala Gly Tyr Lys Pro Asp Glu Gly Lys Arg Gly Asp Ala Cys Glu Gly
1               5                   10                  15

Asp Ser Gly Gly Pro Phe Val
            20

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa at this position may be Glu or Gln
<220> FEATURE:
<221> NAME/KEY: MISC_FEATURE
<222> LOCATION: (11)..(11)
<223> OTHER INFORMATION: Xaa at this position may be Phe, Met, Leu, His
      or Val
```

```
<400> SEQUENCE: 10

Asp Ala Cys Xaa Gly Asp Ser Gly Gly Pro Xaa Val
1               5                   10

<210> SEQ ID NO 11

<400> SEQUENCE: 11

000

<210> SEQ ID NO 12

<400> SEQUENCE: 12

000

<210> SEQ ID NO 13
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at this position may be Ala or Ser
<220> FEATURE:
<221> NAME/KEY: MISC_FEATURE
<222> LOCATION: (4)..(4)
<223> OTHER INFORMATION: Xaa at this position may be Glu or Gln
<220> FEATURE:
<221> NAME/KEY: MISC_FEATURE
<222> LOCATION: (11)..(11)
<223> OTHER INFORMATION: Xaa at this position may be Phe, Met, Leu, His,
      or Val

<400> SEQUENCE: 13

Asp Xaa Cys Xaa Gly Asp Ser Gly Gly Pro Xaa Val
1               5                   10

<210> SEQ ID NO 14
<211> LENGTH: 10
<212> TYPE: PRT
<213> ORGANISM: Homo sapiens

<400> SEQUENCE: 14

Cys Glu Gly Asp Ser Gly Gly Pro Phe Val
1               5                   10

<210> SEQ ID NO 15
<211> LENGTH: 10
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa at this position may be Glu or Gln
<220> FEATURE:
<221> NAME/KEY: MISC_FEATURE
<222> LOCATION: (9)..(9)
<223> OTHER INFORMATION: Xaa at this position may be Phe, Met, Leu, His
      or Val

<400> SEQUENCE: 15

Cys Xaa Gly Asp Ser Gly Gly Pro Xaa Val
1               5                   10
```

```
<210> SEQ ID NO 16
<211> LENGTH: 4
<212> TYPE: PRT
<213> ORGANISM: Homo sapiens

<400> SEQUENCE: 16

Arg Gly Asp Ala
1

<210> SEQ ID NO 17
<211> LENGTH: 14
<212> TYPE: PRT
<213> ORGANISM: Homo sapiens

<400> SEQUENCE: 17

Arg Gly Asp Ala Cys Glu Gly Asp Ser Gly Gly Pro Phe Val
1               5                   10

<210> SEQ ID NO 18
<211> LENGTH: 33
<212> TYPE: PRT
<213> ORGANISM: Homo sapiens

<400> SEQUENCE: 18

Asp Asn Met Phe Cys Ala Gly Tyr Lys Pro Asp Glu Gly Lys Arg Gly
1               5                   10                  15

Asp Ala Cys Glu Gly Asp Ser Gly Gly Pro Phe Val Met Lys Ser Pro
            20                  25                  30

Phe

<210> SEQ ID NO 19
<211> LENGTH: 33
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (20)..(20)
<223> OTHER INFORMATION: Xaa at this position may be Glu or Gln
<220> FEATURE:
<221> NAME/KEY: MISC_FEATURE
<222> LOCATION: (27)..(27)
<223> OTHER INFORMATION: Xaa at this position may be Phe, Met, Leu, His
      or Val

<400> SEQUENCE: 19

Asp Asn Met Phe Cys Ala Gly Tyr Lys Pro Asp Glu Gly Lys Arg Gly
1               5                   10                  15

Asp Ala Cys Xaa Gly Asp Ser Gly Gly Pro Xaa Val Met Lys Ser Pro
            20                  25                  30

Phe

<210> SEQ ID NO 20
<211> LENGTH: 23
<212> TYPE: PRT
<213> ORGANISM: Homo sapiens
<220> FEATURE:
<221> NAME/KEY: misc_feature
<222> LOCATION: (14)..(14)
<223> OTHER INFORMATION: Xaa can be any naturally occurring amino acid

<400> SEQUENCE: 20

Ala Gly Tyr Lys Pro Asp Glu Gly Lys Arg Gly Asp Ala Xaa Glu Gly
1               5                   10                  15
```

```
Asp Ser Gly Gly Pro Phe Val
            20

<210> SEQ ID NO 21
<211> LENGTH: 23
<212> TYPE: PRT
<213> ORGANISM: Homo sapiens

<400> SEQUENCE: 21

Ala Gly Tyr Lys Pro Asp Glu Gly Lys Arg Gly Asp Ala Ala Glu Gly
1               5                   10                  15

Asp Ser Gly Gly Pro Phe Val
            20

<210> SEQ ID NO 22
<211> LENGTH: 23
<212> TYPE: PRT
<213> ORGANISM: Homo sapiens

<400> SEQUENCE: 22

Ala Gly Tyr Lys Pro Asp Glu Gly Lys Arg Gly Asp Ala Ala Glu Gly
1               5                   10                  15

Asp Ser Gly Gly Pro Phe Val
            20

<210> SEQ ID NO 23
<211> LENGTH: 33
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa at this position may be alanine, glycine,
      serine or an S-protected cysteine
<220> FEATURE:
<221> NAME/KEY: MISC_FEATURE
<222> LOCATION: (19)..(19)
<223> OTHER INFORMATION: Xaa at this position may be alanine, glycine,
      serine or an S-protected cysteine

<400> SEQUENCE: 23

Asp Asn Met Phe Xaa Ala Gly Tyr Lys Pro Asp Glu Gly Lys Arg Gly
1               5                   10                  15

Asp Ala Xaa Glu Gly Asp Ser Gly Gly Pro Phe Val Met Lys Ser Pro
            20                  25                  30

Phe

<210> SEQ ID NO 24
<211> LENGTH: 33
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa at this position may be alanine, glycine,
    serine or an S-protected cysteine
<220> FEATURE:
<221> NAME/KEY: MISC_FEATURE
<222> LOCATION: (19)..(19)
<223> OTHER INFORMATION: Xaa at this position may be alanine, glycine,
    serine or an S-protected cysteine
<220> FEATURE:
<221> NAME/KEY: MISC_FEATURE
<222> LOCATION: (20)..(20)
```

```
<223> OTHER INFORMATION: Xaa at this position may be Glu or Gln
<220> FEATURE:
<221> NAME/KEY: MISC_FEATURE
<222> LOCATION: (27)..(27)
<223> OTHER INFORMATION: Xaa at this position may be Phe, Met, Leu, His
      or Val

<400> SEQUENCE: 24

Asp Asn Met Phe Xaa Ala Gly Tyr Lys Pro Asp Glu Gly Lys Arg Gly
1               5                   10                  15
Asp Ala Xaa Xaa Gly Asp Ser Gly Gly Pro Xaa Val Met Lys Ser Pro
            20                  25                  30
Phe

<210> SEQ ID NO 25
<211> LENGTH: 33
<212> TYPE: PRT
<213> ORGANISM: Homo sapiens

<400> SEQUENCE: 25

Asp Asn Met Phe Ala Ala Gly Tyr Lys Pro Asp Glu Gly Lys Arg Gly
1               5                   10                  15
Asp Ala Ala Glu Gly Asp Ser Gly Gly Pro Phe Val Met Lys Ser Pro
            20                  25                  30
Phe

<210> SEQ ID NO 26
<211> LENGTH: 33
<212> TYPE: PRT
<213> ORGANISM: Homo sapiens

<400> SEQUENCE: 26

Asp Asn Met Phe Ala Ala Gly Tyr Lys Pro Asp Glu Gly Lys Arg Gly
1               5                   10                  15
Asp Ala Ala Glu Gly Asp Ser Gly Gly Pro Phe Val Met Lys Ser Pro
            20                  25                  30
Phe

<210> SEQ ID NO 27
<211> LENGTH: 33
<212> TYPE: PRT
<213> ORGANISM: Homo sapiens

<400> SEQUENCE: 27

Ala Gly Tyr Lys Pro Asp Glu Gly Lys Arg Gly Asp Ala Cys Glu Gly
1               5                   10                  15
Asp Ser Gly Gly Pro Phe Val Met Lys Ser Pro Phe Asn Asn Arg Trp
            20                  25                  30
Tyr

<210> SEQ ID NO 28
<211> LENGTH: 33
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (15)..(15)
<223> OTHER INFORMATION: Xaa at this position may be Glu or Gln
<220> FEATURE:
<221> NAME/KEY: MISC_FEATURE
<222> LOCATION: (22)..(22)
```

```
<223> OTHER INFORMATION: Xaa at this position may be Phe, Met, Leu, His
      or Val

<400> SEQUENCE: 28

Ala Gly Tyr Lys Pro Asp Glu Gly Lys Arg Gly Asp Ala Cys Xaa Gly
1               5                   10                  15

Asp Ser Gly Gly Pro Xaa Val Met Lys Ser Pro Phe Asn Asn Arg Trp
            20                  25                  30

Tyr

<210> SEQ ID NO 29
<211> LENGTH: 33
<212> TYPE: PRT
<213> ORGANISM: Homo sapiens

<400> SEQUENCE: 29

Ala Gly Tyr Lys Pro Asp Glu Gly Lys Arg Gly Asp Ala Cys Glu Gly
1               5                   10                  15

Asp Ser Gly Gly Pro Phe Val Met Lys Ser Pro Phe Asn Asn Arg Trp
            20                  25                  30

Tyr

<210> SEQ ID NO 30
<211> LENGTH: 23
<212> TYPE: PRT
<213> ORGANISM: Homo sapiens

<400> SEQUENCE: 30

Ala Gly Tyr Lys Pro Asp Glu Gly Lys Arg Gly Asp Ala Ser Glu Gly
1               5                   10                  15

Asp Ser Gly Gly Pro Phe Val
            20
```

METHODS OF USING THROMBIN DERIVATIVES TO TREAT MEDULLOBLASTOMA

CROSS-REFERENCE TO RELATED APPLICATIONS

This application claims the benefit of U.S. Provisional Application Ser. No. 62/010,553, filed Jun. 11, 2014, which is incorporated by reference herein.

GOVERNMENT FUNDING

This invention was made with government support under HHSN261201300076C, awarded by the National Institutes of Health. The government has certain rights in the invention.

SEQUENCE LISTING

This application contains a Sequence Listing electronically submitted to the United States Patent and Trademark Office via EFS-Web as an ASCII text file entitled "26500860101_ST25.txt" having a size of 10.3 kilobytes and created on Aug. 21, 2015. The information contained in the Sequence Listing is incorporated by reference herein.

BACKGROUND

Brain cancer is the second leading cause of cancer-related deaths in children in the United States, with approximately 5000 new cases each year (Cancer Facts & Figures 2015, Atlanta: American Cancer Society). More specifically, medulloblastoma is the most common malignant brain tumor in children, accounting for 25-30% of primary central nervous system (CNS) tumors (Cancer Facts & Figures 2015, Atlanta: American Cancer Society). Current available treatment protocols for medulloblastomas include surgical removal of the tumor, fractionated radiation therapy (RT) and intensive chemotherapy treatments (Adamski et al., F1000Prime Rep., 2014;6: 56). Although, such an intense treatment regimen yields a promising average 5-year survival rate of 60-80% (Gajjar and Robinson, Nat. Rev. Clin. Oncol., 2014, 11: 714-722), nearly all survivors experience hindered quality of life and long-term cognitive dysfunction due to aggressive RT (Castelo-Branco et al., Pediatr Res., 2012, 71: 523-528). Moreover, one of the most problematic issues stems from the recurrence of the disease which occurs in almost 20% of patients post-treatment, resulting in a 5-year survival rate of less than 5% (Zeltzer et al., J Clin Oncol., 1999, 17: 832-845).

Medulloblastoma is classified as a stage IV primary tumor that originates in the cerebellum (Polkinghorn and Tarbell, Nat. Clin. Pract. Oncol., 2007, 4:295-304). Due to its wide variability in molecular, histological and clinical profiles, medulloblastoma has been classified into 4 unique profiles based on transcriptional studies (Taylor et al., Acta Neuropathol., 2012, 123:465-472). In 2012, an international consensus was reached in naming the four groups, Sonic hedgehog (Shh), Wingless (Wnt), Group C and Group D (Taylor et al., Acta Neuropathol., 2012, 123:465-472). The Shh and Wnt groups are named according to the regulating pathways that cause this specific subtype, while the specific driver mutations for groups C and D remain unknown. Both the Wnt and Shh pathways have been implicated in promoting the development of medulloblastoma during embryogenesis, and targeting these specific signaling molecules have been shown to reduce tumor growth in vivo (Brun et al., Oncogene, 2015, doi:10.1038/onc.2014.304, Matsuo et al., Toxicol. Pathol., 2014, 42:1174-1187, Baryawno et al., Cancer Res., 2010, 70:266-276).

Regardless of the specific signaling pathway involved in medulloblastomas, the underlying cause of this type of cancer seems to arise from the dysregulation of normal stem/progenitor cells during development (Polkinghorn and Tarbell, Nat. Clin. Pract. Oncol., 2007, 4:295-304). In essence, when normal stem cells lose their homeostatic proliferative functions, they develop a mutated phenotype and transform into cancer stem cells (CSCs) (Hope et al., Nat. Immunol., 2004, 5:738-743) which lead to the tumor initiation and progression of medulloblastomas (Manoranjan et al., Pediatr. Res., 2012, 71:516-522).

Cancer stem cells (CSCs) are a subpopulation of cancer cells within tumors with the ability to perpetually self-renew and differentiate, providing tumors with a limitless supply of cancer cells (Jung et al., Arch. Pharm. Res., 2015, 38:414-422). To date, available conventional treatment therapies are only efficient in targeting the tumor bulk and fail to eradicate the tumor-initiating CSCs residing within the bulk. Such therapies allow for the survival of CSCs post-treatment and result in the repopulation of tumors and relapse of the disease. However, if CSCs can be specifically targeted and eradicated with treatment, then tumor recurrence can be eliminated.

Therefore, it is important to develop cancer therapeutics capable of identifying and targeting CSCs to prevent cancer relapse. To date, there are very few drugs available that are capable of distinguishing CSCs from normal stem cells (Chen et al., Acta Pharmacol. Sin., 2013, 34:732-740). In recent years, several laboratories have identified novel cell-surface markers specific to CSCs in breast, colon, brain and prostate cancers (Hu et al., Am. J. Cancer Res., 2012, 2:340-356). More specifically, CD133 (prominin-1), CD44 (cluster of differentiation 44) and LGR5 (leucine-rich repeat containing G protein-coupled receptor 5) CSC markers have all been shown to be associated with tumorigenesis and stemness potential of medulloblastoma (Blazek et al., Int. J. Radiat. Oncol. Biol. Phys., 2007, 67:1-5, Whittier et al., Acta Neuropathol. Commun., 2013, 1:66, Parker et al., Anticancer Res., 2005, 25:3855-3863).

For years, CSCs have been shown to have a unique ability to resist radiation exposure, minimize inflicted radiation-induced damage and evade apoptosis (Rycaj et al., Int. J. Radiat. Biol., 2014, 90:615-621). The radio-resistant property of CSCs is believed to be due to their ability to activate a more rapid DNA repair mechanism compared to normal stem cells, allowing them to escape cellular death (Rycaj et al., Int. J. Radiat. Biol., 2014, 90:615-621). Current brain cancer therapies, such as x-ray and gamma ray ionizing radiation, result in both single stranded and double stranded DNA breaks (Aparicio et al., DNA Repair (Amst), 2014, 19:169-175). Single-stranded breaks (SSBs) are well-tolerated by the cells because the strand is able to ligate and repair itself rapidly. On the other hand, double-stranded breaks (DSBs) are the most biologically lethal type of DNA damage and a major focus for developing novel radiotherapy cancer strategies (Aparicio et al., DNA Repair (Amst), 2014, 19:169-175). Upon radiation-induced DSBs, a DNA damage response signaling cascade is activated and triggers a chain of events which include: 1) identification of the damage, 2) arrest of the cell cycle and 3) DNA repair via non-homologous end joining or homologous recombination (Raleigh and Haas-Kogan, Future Oncol., 2013, 9:219-233). In some cases, cells are damaged to an irreparable extent and are thus prohibited from exiting the cell cycle arrest (Raleigh and Haas-Kogan, Future Oncol., 2013, 9:219-233). Instead, they either undergo apoptosis or initiate cell senescence (Raleigh and Haas-Kogan, Future Oncol., 2013, 9:219-233). However, in the event cells can be repaired, selection and activation of the appropriate repair pathway is dependent on the phase at which the cells were cycling through at the time of the damage.

The NF-κB pathway is a widely studied signaling pathway that is involved in various processes, including inflammation and cancer (Hoesel and Schmid, Mol. Cancer., 2013, 12:86). In normal conditions the NF-κB pathway is tightly regulated and is only activated in response to specific cellular signals (Hoesel and Schmid, Mol. Cancer., 2013, 12:86). When inactive, NF-κB is bound to an inhibitory IκBα complex and remains sequestered in the cytoplasm. Upon cellular stimulus, a signaling cascade is activated in which IκBα (inhibitor of κB) is phosphorylated by IKK (IkB kinase). Phosphorylation of IκBα results in the release of IκBα from NF-κB, thereby activating NF-κB and promoting its translocation into the nucleus. NF-κB then binds to DNA and activates the transcription of various pro-survival genes. In contrast, in CSCs, the NF-κB signaling pathway is deregulated and constitutively active (Hoesel and Schmid, Mol. Cancer., 2013, 12:86). This allows the cells to over proliferate and avoid apoptosis, thereby increasing their radio-resistance and tumorigenic potential (Karin et al., Nat. Rev. Cancer., 2002, 2:301-310, Spiller et al., BMC Cancer. 2011, 11:136). Several laboratories are trying to develop novel NF-κB inhibitors in an attempt to block the transcription of these pro-tumorigenic genes (Pal et al., J. Inflamm. (Lond)., 2014, 11:23, Fuchs et al., Curr. Mol. Pharmacol., 2010, 3: 98-122, Sharma et al., Curr. Med. Chem., 2007, 14:1061-1074).

Thrombin peptide TP508, also known as rusalatide acetate or Chrysalin®, is a 23-amino acid synthetic peptide representing a portion of the human prothrombin with a sequence of AGYKPDEGKRGDACEGDSGGPFV (SEQ ID NO:6). TP508 corresponds to amino acids 508-530 of the prothrombin or 183-200 of the α-thrombin peptide. Thrombin plays an important role in the coagulation cascade by converting soluble fibrinogen into the insoluble fibrin required for blood clot formation (Krishnaswamy, J. Thromb. Haemost., 2013, 11 Suppl 1:265-276). Upon vascular injury, prothrombin is proteolytically cleaved by activated factor X, yielding the biologically active α-thrombin (Krishnaswamy, J. Thromb. Haemost., 2013, 11 Suppl 1:265-276). The biological activity of the TP508 sequence was discovered by screening molecules that could bind to high-affinity thrombin receptors and mimic cellular effects of thrombin at sites of tissue injury (Carney et al., Semin. Thromb. Hemost., 1986, 12:231-240, Glenn et al., Pept. Res., 1988, 1:65-73). Thus, TP508 was selected for its interaction with a subset of high affinity non-proteolytic thrombin receptors (NPARs). Early studies demonstrated specificity of TP508 binding and crosslinking to the NPAR receptor, specific signaling cascades that included activation of endothelial nitric oxide synthase, PI3K, SRC, AKT and PKC.

SUMMARY OF THE APPLICATION

To date there are no FDA approved radiosensitizers available to treat cancers, including medulloblastoma (Raviraj et al., Indian J. Dent. Res., 2014, 25:83-90). In clinical trials, radiosensitizers are being administered prior to treatment in order to render cancer cells more susceptible to radiotherapy, thereby increasing the effectiveness of radiation (Raviraj et al., Indian J. Dent. Res., 2014, 25:83-90). However, current radiosensitizers in clinical trials are only focused at targeting the tumor bulk and not the tumor-initiating CSCs (Katz et al., Int. J. Radiat. Oncol. Biol. Phys., 2009, 73:988-996). Recently, conventional chemotherapy drugs such as 5-Fluorouracil and Gemcitabine have been tested in clinical trials as potential radiosensitizers for cervix, esophagus, and pancreatic cancer (Katz et al., Int. J. Radiat. Oncol. Biol. Phys., 2009, 73:988-996). Although results are promising, these drugs exert numerous side effects on patients, lack the ability to target CSCs, and are not being tested in medulloblastomas (Katz et al., Int. J. Radiat. Oncol. Biol. Phys., 2009, 73:988-996).

In Phase I studies, TP508 was shown to exert protective effects on normal neural stem/progenitor cells, promote neurogenesis, and reduce cognitive dysfunction post-radiotherapy (Kantara et al., Clin. Transl. Res. Forum. 2014). In order to confirm that TP508 did not interfere with tumor shrinkage, TP508 was administered systemically into tumor-bearing mice prior to radiotherapy. Surprisingly, not only did TP508 not interfere with tumor shrinkage, but it actually appeared to target CSCs to tumor shrinkage in vivo. The ability for TP508 to target cancer cells while protecting neuronal cells makes this drug an ideal drug candidate for the development of a novel non-toxic radiosensitizing agent for cancers.

Provided herein are methods for using a thrombin peptide derivative. In one embodiment, the method includes administering to a subject having a medulloblastoma an effective amount of a thrombin peptide derivative, and exposing cells of the medulloblastoma of the subject to a cancer treatment after administering the thrombin peptide derivative to the subject. Viability of cells of the medulloblastoma is decreased compared to viability of cells of the medulloblastoma before the administering and the exposing. In one embodiment, the cells of the medulloblastoma having decreased viability include cancer stem cells.

In one embodiment, the method includes administering to a subject having a medulloblastoma an effective amount of a thrombin peptide derivative, and exposing cells of the medulloblastoma of the subject to a cancer treatment after administering the thrombin peptide derivative to the subject. Shrinkage of the medulloblastoma in the subject is increased compared to shrinkage of the medulloblastoma before the administering and the exposing.

The thrombin peptide derivative may be administered between 1 hour and 60 hours before the exposing. The administration of the thrombin peptide derivative may be systemic, such as intravenous. The subject may be a child, a young adult, or an adult. In one embodiment, the medulloblastoma is a relapse following an initial treatment. The cancer treatment may include therapeutic radiation, chemotherapy, or a combination thereof.

In one embodiment, the method includes contacting a medulloblastoma cancer cell with an effective amount of a thrombin peptide derivative, and exposing the medulloblastoma cancer cell to a cancer treatment after contacting the medulloblastoma cancer cell with the thrombin peptide derivative. Viability of the medulloblastoma cancer cell is decreased compared to the viability of the medulloblastoma cancer before the contacting and the exposing. In one embodiment, the medulloblastoma cancer cell is ex vivo, and in another embodiment the medulloblastoma cancer cell is in vivo. In one embodiment, the medulloblastoma cancer cell is a cancer stem cell. In one embodiment, the thrombin peptide derivative may be administered between 1 hour and 60 hours before the exposing. When the medulloblastoma cancer cell is in vivo, the thrombin peptide derivative may be administered, for instance systemically, such as by intravenous injection. The subject may be a child, a young adult, or an adult. The cancer treatment may include therapeutic radiation, chemotherapy, or a combination thereof.

The thrombin peptide derivative includes Asp-Ala-R, wherein R is a serine esterase conserved sequence. In one embodiment, the thrombin peptide derivative is a polypeptide 12 to 23 amino acid residues in length comprising the sequence Arg-Gly-Asp-Ala (SEQ ID NO: 16) and a serine esterase conserved sequence. In one embodiment, the serine esterase conserved sequence includes the sequence Cys-$X_1$-Gly-Asp-Ser-Gly-Gly-Pro-$X_2$-Val (SEQ ID NO:15), wherein $X_1$ is Glu or Gln and $X_2$ is Phe, Met, Leu, His or Val. In one embodiment, the thrombin peptide derivative includes the sequence Ala-Gly-Tyr-Lys-Pro-Asp-Glu-Gly-Lys-Arg-Gly-Asp-Ala-Cys-$X_1$-Gly-Asp-Ser-Gly-Gly-Pro-$X_2$-Val (SEQ ID NO:2), an N-terminal truncated fragment thereof comprising at least fourteen amino acid residues, or a C-terminal truncated fragment thereof comprising at least eighteen amino acid residues, wherein $X_1$ is Glu or Gln and $X_2$ is Phe, Met, Leu, His or Val. In one embodiment, the thrombin peptide derivative is H-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-$NH_2$ (SEQ ID NO:3). In one embodiment, the thrombin peptide derivative includes the polypeptide Arg-Gly-Asp-Ala-Xaa-$X_1$-Gly-Asp-Ser-Gly-Gly-Pro-$X_2$-Val (SEQ ID NO:4), wherein Xaa is alanine, glycine, serine or an S-protected cysteine; $X_1$ is Glu or Gln; and $X_2$ is Phe, Met, Leu, His or Val. In one embodiment, the thrombin derivative includes a C-terminal amide, an acylated N-terminus, or a combination thereof, wherein said C-terminal amide is represented by —C(O)$NR_aR_b$, wherein $R_a$ and $R_b$ are independently hydrogen, an aliphatic group comprising up to 10 carbon atoms, or $R_a$ and $R_b$, taken together with the nitrogen to which they are bonded, form a $C_3$-$C_{10}$ non-aromatic heterocyclic group, and wherein said N-terminal acyl group is represented by $R_cC(O)$—, where $R_c$ is hydrogen, an aliphatic group comprising up to 10 carbon atoms or a phenyl group optionally substituted with one or more groups selected from $C_1$-$C_6$ alkyl, $C_1$-$C_6$ alkoxy, $C_1$-$C_6$ haloalkyl, $C_1$-$C_6$ haloalkoxy, nitro and cyano.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 2. TP508 decreases cell viability, tumor heterogeneity and relapse potential of medulloblastoma cancer cells in vitro, post-RT. FIG. 2Bii: Relapse potential of cancer stem cells treated with RT±TP508. FIG. 2C, Number of secondary spheroids formed post-RT±TP508.

FIG. 3. TP508 decreases the expression and proliferation of cancer stem cells while increasing apoptosis.

FIG. 4. TP508 inhibits the growth of Daoy medulloblastoma tumor xenografts in vivo.

DETAILED DESCRIPTION OF ILLUSTRATIVE EMBODIMENTS

Figure 1:
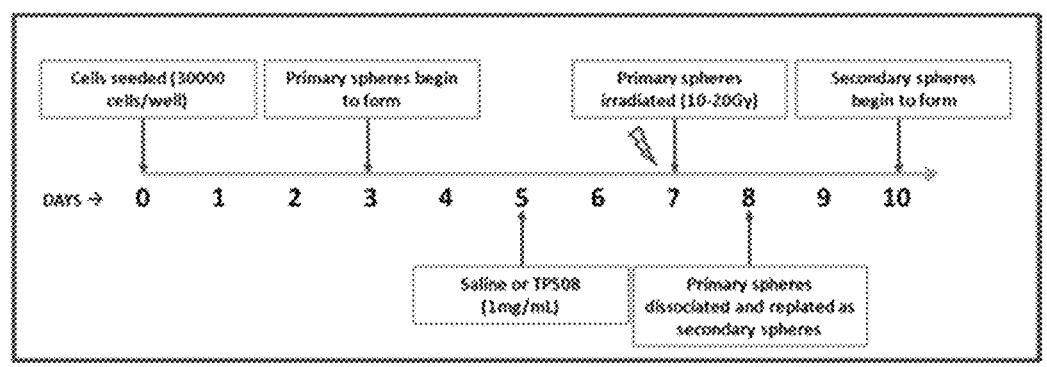
FIG. 1. Schematic depicting the steps of treatment of brain cancer neurospheres/spheroids in vitro.

The inventors have used human medulloblastoma Daoy cells to form primary spheroids/neurospheres, a commonly accepted model for selection of cancer stem cells, to analyze the effects of exposing cells to a thrombin peptide derivative. The inventors have determined that pre-treatment of primary spheroids with an effective amount of a thrombin peptide derivative before exposing the primary spheroids to radiation therapy sensitizes the medulloblastoma cells and/or medulloblastoma stem cells to the therapeutic radiation, resulting in greater medulloblastoma cell death. It is expected that pre-treatment using thrombin peptide derivatives will also sensitize medulloblastoma cells when combined with chemotherapeutic agents. The pre-treatment also reduces or delays the potential for tumor relapse following the radiation therapy.

Prior experiments with thrombin peptide derivatives have demonstrated protection of normal brain tissues and activation of neural stem cells to prevent long-term damage to brain following radiation exposure (Carney, US Published Patent Application 20130101574), which may suggest that thrombin peptide derivatives would have a protective effect on cancer cells, such as cancer stem cells. However, the results disclosed herein that thrombin peptide derivatives sensitize medulloblastoma cells and/or medulloblastoma stem cells to apoptotic effects of radiation therapy are unexpected. Further, the pre-treatment with thrombin peptide derivatives was found to be dependent upon the time of administration. Using an in vitro model, pre-treatment at 1 hour or 24 hours before radiation therapy resulted in a three day delay in the formation of secondary spheroids, but by 4 days there was no difference between pre-treated and non-treated control cells. Further, treatment with a thrombin peptide derivative after the radiation treatment had no effect on the formation of secondary spheroids. In contrast, pre-treatment at 48 hours before therapeutic radiation surprisingly resulted in a statistically significant delay in the formation of secondary spheroids for at least 7 days.

Methods of Use

The method includes contacting a medulloblastoma cancer cell with an effective amount of a thrombin peptide derivative, and exposing the medulloblastoma cancer cell to a cancer treatment such as radiation, chemotherapy, or a combination thereof. The medulloblastoma cancer cell may be a cancer stem cell. The medulloblastoma cancer cell may be ex vivo or in vivo. As used herein, "ex vivo" refers to a cell that has been removed from the body of an animal. Ex vivo cells include, for instance, primary cells (e.g., cells that have recently been removed from a subject and are capable of limited growth in tissue culture medium), and cultured cells (e.g., cells that are capable of long term culture in tissue culture medium). As used herein, "in vivo" refers to a cell that is present within the body of an animal. The use of a thrombin peptide derivative sensitizes a medulloblastoma cancer cell, such as cancer stem cell, to a cancer treatment such as radiation. Thus, the method can result in decreased viability of a medulloblastoma cancer cell, reduced ability of a cancer stem cell to repair DNA damage from radiation exposure, down-regulated activation of NF-kB in a medulloblastoma cancer cell, or a combination thereof.

In one embodiment, the method includes administering to the subject an effective amount of a thrombin peptide derivative, and exposing cells of the medulloblastoma to therapeutic cancer treatment, such as radiation, chemotherapy, or a combination thereof. In one embodiment, the methods disclosed herein include treating one or more symptoms or clinical signs of a medulloblastoma in a subject. As used herein, the term "symptom" refers to subjective evidence of a medulloblastoma experienced by the subject and caused by the cancer. As used herein, the term "clinical sign" or, simply, "sign" refers to objective evidence of medulloblastoma caused by the cancer. Symptoms and/or clinical signs associated with medulloblastoma and the evaluations of such symptoms and/or clinical signs are routine and known in the art. The use of a thrombin peptide derivative sensitizes the cancer cells, such as cancer stem cells, to a cancer treatment such as radiation, chemotherapy, or a combination thereof. Thus, the method can result in decreased viability of cancer cells of the tumor, such as cancer stem cells, increased remission of the medulloblastoma, decreased tumor growth, increased tumor shrinkage, decreased frequency of metastasis, decreased tumor relapse, increased cancer survival rate of the subject, or a combination thereof, compared to the subject exposed to the therapeutic cancer treatment and not administered the thrombin peptide derivative. Remission of the medulloblastoma may be partial (e.g., decrease or disappearance of some symptoms or signs) or complete (e.g., decrease or disappearance of and symptoms and signs). The subject may have been treated for medulloblastoma previously, for instance, the subject may have been in remission and the methods des.

Administration of a thrombin peptide derivative described herein can be performed during or after the occurrence of the symptoms and/or clinical signs described herein. Treatment initiated after the development of a medulloblastoma may result in decreasing the severity of symptoms and/or clinical signs, or completely removing the symptoms and/or clinical signs. An "effective amount" of a thrombin peptide derivative is an amount effective to prevent the manifestation of symptoms and/or clinical signs of a medulloblastoma, decrease the severity of the symptoms and/or clinical signs of a medulloblastoma, and/or completely remove the symptoms and/or clinical signs, compared to the absence of pre-treatment with the thrombin peptide derivative. The amount of the thrombin peptide derivative administered will depend on the degree, severity, and stage of the cancer, the amount of therapy desired, and the release characteristics of the pharmaceutical formulation. It will also depend on the subject's health, size, weight, age, sex and tolerance to drugs. In one embodiment, an effective amount results in exposing the cells to a thrombin peptide derivative at a concentration of at least 10 milligram per kilogram (mg/kg), at least 25 mg/kg, at least 50 mg/kg, at least 75 mg/kg, or at least 100 mg/kg bodyweight of the subject.

As used herein, "therapeutic radiation" and "radiation therapy" refer to radiation delivered in a dose high enough to have a cytotoxic effect on cells exposed to the radiation. Methods for administering the radiation therapy are known to the person skilled in the art. The methods described herein are not intended to be limited by the type of radiation therapy. Thus, the therapeutic radiation may include ionizing radiation, and may be delivered using a single source, or by multiple sources that intersect at the tumor. The therapeutic radiation may be a high level single exposure or a fractioned exposure (given in lower repeated dosages to aid in avoiding killing of normal tissues). In one embodiment, an effective dose of radiation is any dose of radiation effective to kill cells. For instance, in one embodiment an effective dose of radiation used in the treatment of medulloblastoma and other tumors is 30 gray (Gy) given in 5 daily fractions of 6 Gy, or up to 72 Gy given in 35 fractions over a period of 7 weeks. In one embodiment, the pre-treatment using a thrombin peptide derivative can permit a decrease in the therapeutic radiation. For instance, the use of a thrombin peptide derivative may permit the dose of radiation to be decreased and/or the duration of the exposure to be decreased when compared to the dose used when a thrombin peptide derivative is not administered.

As used herein, "chemotherapy" refer to therapy involving the use of anticancer drugs, e.g., chemotherapeutic agents, that kill rapidly dividing cells, such as cancer cells. Chemotherapeutic agents are known to the art and routinely used as a treatment for cancer. Methods for administering chemotherapeutic agents are known to the person skilled in the art. The methods described herein are not intended to be limited by the type of chemotherapeutic agent used.

It is expected that pre-treatment using thrombin peptide derivatives will also sensitize medulloblastoma cells to treatment with chemotherapeutic agents. Methods for administering chemotherapeutic agents are known to the person skilled in the art, as are chemotherapeutic agents that can be used to treat a medulloblastoma. The methods described herein are not intended to be limited by the type of chemotherapy. In one embodiment, the pre-treatment using a thrombin peptide derivative can permit a decrease in the chemotherapeutic agent. For instance, the dose of chemotherapeutic agent may be decreased and/or the duration of the exposure may be decreased.

A thrombin derivative peptide is used before exposure of a cell or a subject to a cancer treatment, such as radiation. In one embodiment, use of the thrombin peptide derivative, including administration of the thrombin peptide derivative, may be at least 1 hour, at least 5 hours, at least 10 hours, at least 15 hours, at least 20 hours, at least 24 hours, at least 36 hours, at least 42 hours, at least 48 hours, or at least 56 hours before the onset of a cancer treatment, such as radiation therapy. In one embodiment, use of the thrombin peptide derivative, including administration of the thrombin peptide derivative, may be no greater than 72 hours, no greater than 66 hours, no greater than 60 hours, no greater than 54 hours, no greater than 48 hours, no greater than 42 hours, no greater than 36 hours, no greater than 24 hours before the onset cancer treatment, such as radiation therapy. In one embodiment, there is no upper limit on when the thrombin derivative peptide is administered before the radiation. In one embodiment, the administration of the thrombin peptide derivative is between 24 hours and 48 hours before the onset of cancer treatment, such as radiation therapy.

The subject may be any age. In one embodiment, the subject is a child or young adult (birth through 19 years), or an adult.

Thrombin Derivative Peptides

Thrombin peptide derivatives (also referred to herein as thrombin derivative peptides) are analogs of thrombin that have an amino acid sequence derived at least in part from thrombin and are active at the non-proteolytically activated thrombin receptor (NPAR). Thrombin peptide derivatives can include, for example, peptides that are produced by recombinant DNA methods, peptides produced by enzymatic digestion of thrombin, and peptides produced synthetically, which can include amino acid substitutions compared to thrombin and/or modified amino acids, especially at one or both termini.

Thrombin peptide derivatives provided herein include thrombin derivative peptides described in U.S. Pat. Nos. 5,352,664 and 5,500,412. In one embodiment, the thrombin peptide derivative is a thrombin peptide derivative or a physiologically functional equivalent, i.e., a polypeptide with no more than about fifty amino acids, preferably no more than about thirty amino acids and having sufficient homology to the fragment of human thrombin corresponding to thrombin amino acids 508-530 (Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val; SEQ ID NO:6) that the polypeptide activates NPAR.

In another embodiment, the thrombin peptide derivative is a thrombin peptide derivative including a moiety represented by Structural Formula (I):

Asp-Ala-R    (I).

R is a serine esterase conserved domain. Serine esterases, e.g., trypsin, thrombin, chymotrypsin and the like, have a region that is highly conserved. "Serine esterase conserved domain" refers to a polypeptide having the amino acid sequence of one of these conserved regions or is sufficiently homologous to one of these conserved regions such that the thrombin peptide derivative retains NPAR activating ability.

A physiologically functional equivalent of a thrombin derivative encompasses molecules which differ from thrombin derivatives in aspects which do not affect the function of the thrombin receptor binding domain or the serine esterase conserved amino acid sequence. Such aspects may include, but are not limited to, conservative amino acid substitutions (as defined below) and modifications, for example, amidation of the carboxyl terminus, acetylation of the amino terminus, conjugation of the polypeptide to a physiologically inert carrier molecule, sequence alterations in accordance with the serine esterase conserved sequences, or a combination thereof.

In one embodiment, a domain having a serine esterase conserved sequence can include a polypeptide sequence containing at least 4-12 of the N-terminal amino acids of the dodecapeptide previously shown to be highly conserved among serine proteases (Asp-$X_1$-Cys-$X_2$-Gly-Asp-Ser-Gly-Gly-Pro-$X_3$-Val; SEQ ID NO:13); wherein $X_1$, is either Ala or Ser; $X_2$ is either Glu or Gln; and $X_3$ is Phe, Met, Leu, His, or Val).

In one embodiment, the serine esterase conserved sequence includes the amino acid sequence of SEQ ID NO:14 (Cys-Glu-Gly-Asp-Ser-Gly-Gly-Pro-Phe-Val) or a C-terminal truncated fragment of a polypeptide having the amino acid sequence of SEQ ID NO:14. It is understood, however, that zero, one, two or three amino acids in the serine esterase conserved sequence can differ from the corresponding amino acid in SEQ ID NO:14. Preferably, the amino acids in the serine esterase conserved sequence which differ from the corresponding amino acid in SEQ ID NO:14 are conservative substitutions as defined below, and are more preferably highly conservative substitutions.

In another embodiment, the serine esterase conserved sequence includes the amino acid sequence of SEQ ID NO:15 (Cys-$X_1$-Gly-Asp-Ser-Gly-Gly-Pro-$X_2$-Val; $X_1$ is Glu or Gln and $X_2$ is Phe, Met, Leu, His or Val) or a C-terminal truncated fragment thereof having at least six amino acids, preferably at least nine amino acids.

In a preferred embodiment, the thrombin peptide derivative includes a serine esterase conserved sequence and a polypeptide having a more specific thrombin amino acid sequence Arg-Gly-Asp-Ala (SEQ ID NO:16). One example of a thrombin peptide derivative of this type includes Arg-Gly-Asp-Ala-Cys-$X_1$-Gly-Asp-Ser-Gly-Gly-Pro-$X_2$-Val (SEQ ID NO: 1). $X_1$ and $X_2$ are as defined above for SEQ ID NO:15. The thrombin peptide derivative can include the amino acid sequence of SEQ ID NO:6 (Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val) or an N-TERMINAL truncated fragment thereof, provided that zero, one, two or three amino acids at positions 1-9 in the thrombin peptide derivative differ from the amino acid at the corresponding position of SEQ ID NO:6. Preferably, the amino acid residues in the thrombin peptide derivative which differ from the corresponding amino acid residues in SEQ ID NO:6 are conservative substitutions as defined below, and are more preferably highly conservative substitutions.

Optionally, the thrombin peptide derivatives described herein can be amidated at the C-terminus and/or acylated at the N-terminus. In a specific embodiment, the thrombin peptide derivatives include a C-terminal amide and optionally include an acylated N-terminus, wherein said C-terminal amide is represented by —C(O)NR$_a$R$_b$, wherein R$_a$ and R$_b$ are independently hydrogen, a C$_1$-C$_{10}$ substituted or unsubstituted aliphatic group, or R$_a$ and R$_b$, taken together with the nitrogen to which they are bonded, form a C1-C10 non-aromatic heterocyclic group, and said N-terminal acyl group is represented by R$_c$C(O)—, wherein R$_c$ is hydrogen, a C$_1$-C$_{10}$ substituted or unsubstituted aromatic group, or a C$_1$-C$_{10}$ substituted or unsubstituted aromatic group. In another specific embodiment, the N-terminus of the thrombin peptide derivative is free (i.e., unsubstituted) and the C-terminus is free (i.e., unsubstituted) or amidated, preferably as a carboxamide (i.e., —C(O)NH$_2$). In a specific embodiment, the thrombin peptide derivative includes the following amino acid sequence: Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:6). In another specific embodiment, the thrombin peptide derivative includes the amino sequence of Arg-Gly-Asp-Ala-Cys-Glu-Gly-Asp-Ser-Gly-Gly-Pro-Phe-Val (SEQ ID NO:17). Alternatively, the thrombin peptide derivative includes the amino acid sequence of SEQ ID NO:18: Asp-Asn-Met-Phe-Cys-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-Met-Lys-Ser-Pro-Phe. The thrombin peptide derivates including the amino acids of SEQ ID NO:6, 17, or 18 can optionally be amidated at the C-terminus and/or acylated at the N-terminus. Preferably, the N-terminus is free (i.e., unsubstituted) and the C-terminus is free (i.e., unsubstituted) or amidated, preferably a carboxamide (i.e., —C(O)NH$_2$). It is understood, however, that zero, one, two or three amino acids at positions 1-9 and 14-23 in the thrombin peptide derivative can differ from the corresponding amino acid in SEQ ID NO:6. It is also understood that zero, one, two or three amino acids at positions 1-14 and 19-33 in the thrombin peptide derivative can differ from the corresponding amino acid in SEQ ID NO:18. Preferably, the amino acids in the thrombin peptide derivative which differ from the corresponding amino acid in SEQ ID NO:6 or SEQ ID NO:18 are conservative substitutions as defined below, and are more preferably highly conservative substitutions. Alternatively, an N-terminal truncated fragment of the thrombin peptide derivative having at least fourteen amino acids or a C-terminal truncated fragment of the thrombin peptide derivative having at least eighteen amino acids can be used in the methods provided herein.

A "C-terminal truncated fragment" refers to a fragment remaining after removing an amino acid or block of amino acids from the C-terminus. In one embodiment, a "C-terminal truncated fragment" has at least six amino acids, and more preferably at least nine amino acids. An "N-terminal truncated fragment" refers to a fragment remaining after removing an amino acid or block of amino acids from the N-terminus. In one embodiment, the block of amino acids is no more than three amino acids, more preferably no more than six amino acids. It is to be understood that the terms "C-terminal truncated fragment" and "N-terminal truncated fragment" encompass acylation at the N-terminus and/or amidation at the C-terminus, as described above.

A preferred thrombin peptide derivative for use in the disclosed methods includes the amino acid sequence SEQ ID NO:2: Ala-Gly-Tyr-Lys-Pro-Asp-Glu-Gly-Lys-Arg-Gly-Asp-Ala-Cys-X$_1$-Gly-Asp-Ser-Gly-Gly-Pro-X$_2$-Val. Another preferred thrombin peptide derivative for use in the disclosed methods includes the amino acid sequence of SEQ ID NO:19: Asp-Asn-Met-Phe-Cys-Ala-Gly-Tyr-Lys-Pro-Asp-Glu-Gly-Lys-Arg-Gly-Asp-Ala-Cys-X$_1$-Gly-Asp-Ser-Gly-Gly-Pro-X$_2$-Val-Met-Lys-Ser-Pro-Phe. X$_1$ is Glu or Gln; X$_2$ is Phe, Met, Leu, His or Val. The thrombin peptide derivatives of SEQ ID NO:2 and SEQ ID NO:19 can optionally include a C-terminal amide and/or acylated N-terminus, as defined above. Preferably, the N-terminus is free (i.e., unsubstituted) and the C-terminus is free (i.e., unsubstituted) or amidated, preferably as a carboxamide (i.e., —C(O)NH$_2$). Alternatively, N-terminal truncated fragments of these preferred thrombin peptide derivatives, the N-terminal truncated fragments having at least fourteen amino acids, or C-terminal truncated fragments of these preferred thrombin peptide derivatives, the C-truncated fragments having at least eighteen amino acids, can also be used in the disclosed method.

TP508 is an example of a thrombin peptide derivative and is 23 amino acid residues long, wherein the N-terminal amino acid residue Ala is unsubstituted and the COOH of the C-terminal amino acid Val is modified to an amide represented by —C(O)NH$_2$ (SEQ ID NO:3). Another example of a thrombin peptide derivative includes the amino acid sequence of SEQ ID NO:6, wherein both N- and C-termini are unsubstituted ("deamide TP508"). Other examples of thrombin peptide derivatives which can be used in the disclosed method include N-terminal truncated fragments of TP508 (or deamide TP508), the N-terminal truncated fragments having at least fourteen amino acids, or C-TERMINAL truncated fragments of TP508 (or deamide TP508), the C-terminal truncated fragments having at least eighteen amino acids.

As used herein, a "conservative substitution" in a polypeptide is the replacement of an amino acid with another amino acid that has the same net electronic charge and approximately the same size and shape. Amino acids with aliphatic or substituted aliphatic amino acid side chains have approximately the same size when the total number of carbon and heteroatoms in their side chains differs by no more than about four. They have approximately the same shape when the number of branches in their side chains differs by no more than one. Amino acids with phenyl or substituted phenyl groups in their side chains are considered to have about the same size and shape. Listed below are five groups of amino acids. Replacing an amino acid in a polypeptide with another amino acid from the same group results in a conservative substitution:

Group I: glycine, alanine, valine, leucine, isoleucine, serine, threonine, cysteine, and non-naturally occurring amino acids with C1-C4 aliphatic or C1-C4 hydroxyl substituted aliphatic side chains (straight chained or monobranched).

Group II: glutamic acid, aspartic acid and non-naturally occurring amino acids with carboxylic acid substituted C1-C4 aliphatic side chains (unbranched or one branch point).

Group III: lysine, ornithine, arginine and non-naturally occurring amino acids with amine or guanidino substituted C1-C4 aliphatic side chains (unbranched or one branch point).

Group IV: glutamine, asparagine and non-naturally occurring amino acids with amide substituted C1-C4 aliphatic side chains (unbranched or one branch point).

Group V: phenylalanine, phenylglycine, tyrosine and tryptophan.

As used herein, a "highly conservative substitution" in a polypeptide is the replacement of an amino acid with another amino acid that has the same functional group in the side chain and nearly the same size and shape. Amino acids with aliphatic or substituted aliphatic amino acid side chains have nearly the same size when the total number of carbon and heteroatoms in their side chains differs by no more than two. They have nearly the same shape when they have the same number of branches in their side chains. Examples of highly conservative substitutions include valine for leucine, threonine for serine, aspartic acid for glutamic acid and phenylglycine for phenylalanine Examples of substitutions which are not highly conservative include alanine for valine, alanine for serine and aspartic acid for serine.

Modified Thrombin Peptide Derivatives

In one embodiment of the invention, the thrombin peptide derivatives are modified relative to the thrombin peptide derivatives described above, wherein cysteine residues of aforementioned thrombin peptide derivatives are replaced with amino acids having similar size and charge properties to minimize dimerization of the peptides. Examples of suitable amino acids include alanine, glycine, serine, or an S'-protected cysteine. Preferably, cysteine is replaced with alanine. The modified thrombin peptide derivatives have about the same biological activity as the unmodified thrombin peptide derivatives (Carney, U.S. Pat. No. 7,713,934).

It will be understood that the modified thrombin peptide derivatives disclosed herein can optionally include C-terminal amides and/or N-terminal acyl groups, as described above. Preferably, the N-terminus of a thrombin peptide derivative is free (i.e., unsubstituted) and the C-terminus is free (i.e., unsubstituted) or amidated, preferably as a carboxamide (i.e., —C(O)NH$_2$).

In a specific embodiment, the modified thrombin peptide derivative includes a polypeptide having the amino acid sequence of SEQ ID NO:4: Arg-Gly-Asp-Ala-Xaa-X$_1$-Gly-Asp-Ser-Gly-Gly-Pro-X$_2$-Val, or a C-terminal truncated fragment thereof having at least six amino acids. In one embodiment, the thrombin peptide derivative includes the amino acid sequence of SEQ ID NO:20: Ala-Gly-Tyr-Lys-Pro-Asp-Glu-Gly-Lys-Arg-Gly-Asp-Ala-Xaa-Glu-Gly-Asp-Ser-Gly-Gly-Pro-Phe-Val or a fragment thereof including amino acids 10-18 of SEQ ID NO:20. In one embodiment, the thrombin peptide derivative includes the amino acid sequence SEQ ID NO:5: Ala-Gly-Tyr-Lys-Pro-Asp-Glu-Gly-Lys-Arg-Gly-Asp-Ala-Xaa-X$_1$-Gly-Asp-Ser-Gly-Gly-Pro-X$_2$-Val, or a fragment thereof including amino acids 10-18 of SEQ ID NO:5. Xaa is alanine, glycine, serine or an S-protected cysteine. X$_1$ is Glu or Gln and X$_2$ is Phe, Met, Leu, His or Val. Preferably X$_1$ is Glu, X$_2$ is Phe, and Xaa is alanine One example of a thrombin peptide derivative of this type is a polypeptide having the amino acid sequence Ala-Gly-Tyr-Lys-Pro-Asp-Glu-Gly-Lys-Arg-Gly-Asp-Ala-Ala-Glu-Gly-Asp-Ser-Gly-Gly-Pro-Phe-Val (SEQ ID NO:21). A further example of a thrombin peptide derivative of this type is the polypeptide H-Ala-Gly-Tyr-Lys-Pro-Asp-Glu-Gly-Lys-Arg-Gly-Asp-Ala-Ala-Glu-Gly-Asp-Ser-Gly-Gly-Pro-Phe-Val-NH$_2$ (SEQ ID NO:22). Another example of a thrombin peptide derivative of this type is the polypeptide H-Ala-Gly-Tyr-Lys-Pro-Asp-Glu-Gly-Lys-Arg-Gly-Asp-Ala-Ser-Glu-Gly-Asp-Ser-Gly-Gly-Pro-Phe-Val-NH$_2$ (SEQ ID NO:30) Zero, one, two or three amino acids in the thrombin peptide derivative differ from the amino acid at the corresponding position of SEQ ID NO:4, 20, 5, 21 or 22, provided that Xaa is alanine, glycine, serine or an S-protected cysteine. Preferably, the difference is conservative as defined below.

In another specific embodiment, the thrombin peptide derivative includes a polypeptide having the amino acid sequence SEQ ID NO:23: Asp-Asn-Met-Phe-Xbb-Ala-Gly-Tyr-Lys-Pro-Asp-Glu-Gly-Lys-Arg-Gly-Asp-Ala-Xaa-Glu-Gly-Asp-Ser-Gly-Gly-Pro-Phe-Val-Met-Lys-Ser-Pro-Phe, or a fragment thereof including amino acids 6-28. More preferably, the thrombin peptide derivative includes a polypeptide having the amino acid sequence SEQ ID NO:24: Asp-Asn-Met-Phe-Xbb-Ala-Gly-Tyr-Lys-Pro-Asp-Glu-Gly-Lys-Arg-Gly-Asp-Ala-Xaa-X$_1$-Gly-Asp-Ser-Gly-Gly-Pro-X$_2$-Val-Met-Lys-Ser-Pro-Phe, or a fragment thereof including amino acids 6-28. Xaa and Xbb are independently alanine, glycine, serine or an S-protected cysteine. X$_1$ is Glu or Gln and X$_2$ is Phe, Met, Leu, His or Val. Preferably X$_1$ is Glu, X$_2$ is Phe, and Xaa and Xbb are alanine One example of a thrombin peptide derivative of this type is a polypeptide including the amino acid sequence Asp-Asn-Met-Phe-Ala-Ala-Gly-Tyr-Lys-Pro-Asp-Glu-Gly-Lys-Arg-Gly-Asp-Ala-Ala-Glu-Gly-Asp-Ser-Gly-Gly-Pro-Phe-Val-Met-Lys-Ser-Pro-Phe (SEQ ID NO:25). A further example of a thrombin peptide derivative of this type is the polypeptide H-Asp-Asn-Met-Phe-Ala-Ala-Gly-Tyr-Lys-Pro-Asp-Glu-Gly-Lys-Arg-Gly-Asp-Ala-Ala-Glu-Gly-Asp-Ser-Gly-Gly-Pro-Phe-Val-Met-Lys-Ser-Pro-Phe-NH$_2$ (SEQ ID NO:26). Zero, one, two or three amino acids in the thrombin peptide derivative can differ from the amino acid at the corresponding position of SEQ ID NO:23, 24, 25 or 26. Xaa and Xbb are independently alanine, glycine, serine or an S-protected cysteine. Preferably, the difference is conservative as in conservative substitutions of the thrombin peptide derivatives.

An "S-protected cysteine" is a cysteine residue in which the reactivity of the thiol moiety, —SH, is blocked with a protecting group. Suitable protecting groups are known in the art and are disclosed, for example, in T. W. Greene and P. G. M. Wuts, *Protective Groups in Organic Synthesis*, 3$^{rd}$ Edition, John Wiley & Sons, (1999), pp. 454-493. Suitable protecting groups should be non-toxic, stable in pharmaceutical formulations and have minimum additional functionality to maintain the activity of the thrombin peptide derivative. A free thiol can be protected as a thioether, a thioester, or can be oxidized to an unsymmetrical disulfide. Preferably the thiol is protected as a thioether. Suitable thioethers include, but are not limited to, S-alkyl thioethers (e.g., C$_1$-C$_5$ alkyl), and S-benzyl thioethers (e.g, cysteine-S—S-t-Bu). Preferably the protective group is an alkyl thioether. More preferably, the S-protected cysteine is an S-methyl cysteine. Alternatively, the protecting group can be: 1) a cysteine or a cysteine-containing peptide (the "protecting peptide") attached to the cysteine thiol group of the thrombin peptide derivative by a disulfide bond; or 2) an amino acid or peptide ("protecting peptide") attached by a thioamide bond between the cysteine thiol group of the thrombin peptide derivative and a carboxylic acid in the protecting peptide (e.g., at the C-terminus or side chain of aspartic acid or glutamic acid). The protecting peptide can be physiologically inert (e.g., a polyglycine or polyalanine of no more than about fifty amino acids optionally interrupted by a cysteine), or can have a desirable biological activity.

Thrombin Peptide Derivative Dimers

In some embodiments, the thrombin peptide derivatives of the methods are thrombin peptide derivative dimers (Carney, U.S. Pat. No. 7,456,250. The dimers essentially do not revert to monomers and still have about the same biological activity as the thrombin peptide derivatives monomer described above. A "thrombin peptide derivative dimer" is a molecule including two thrombin peptide derivatives linked by a covalent bond, preferably a disulfide bond between cysteine residues. Thrombin peptide derivative dimers are typically essentially free of the corresponding monomer, e.g., greater than 95% free by weight and preferably greater than 99% free by weight. Preferably the polypeptides are the same and covalently linked through a disulfide bond.

The thrombin peptide derivative dimers provided herein include the thrombin peptide derivatives described above. Specifically, thrombin peptide derivatives have less than about fifty amino acids, preferably less than about thirty-three amino acids. Thrombin peptide derivatives also have sufficient homology to the fragment of human thrombin corresponding to thrombin amino acid residues 508-530: Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:6) so that the polypeptide activates NPAR.

In a specific embodiment, each thrombin peptide derivative including a dimer includes a polypeptide having the amino acid sequence SEQ ID NO:1: Arg-Gly-Asp-Ala-Cys-X$_1$-Gly-Asp-Ser-Gly-Gly-Pro-X$_2$-Val, or a C-terminal truncated fragment thereof including at least six amino acids. More specifically, each thrombin peptide derivative includes the amino acid sequence of SEQ ID NO:6: Ala-Gly-Tyr- Lys-Pro-Asp-Glu-Gly-Lys-Arg-Gly-Asp-Ala-Cys-Glu-Gly-Asp-Ser-Gly-Gly-Pro-Phe-Val, or a fragment thereof including amino acids 10-18 of SEQ ID NO. 5. Even more specifically, the thrombin peptide derivative includes the amino acid sequence SEQ ID NO:2: Ala-Gly-Tyr-Lys-Pro-Asp-Glu-Gly-Lys-Arg-Gly-Asp-Ala-Cys-$X_1$-Gly-Asp-Ser-Gly-Gly-Pro-$X_2$-Val, or a fragment thereof including amino acids 10-18 of SEQ ID NO:2. $X_1$ is Glu or Gln and $X_2$ is Phe, Met, Leu, His or Val. Preferably $X_1$ is Glu, and $X_2$ is Phe. One example of a thrombin peptide derivative of this type is a polypeptide including the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:6). A further example of a thrombin peptide derivative of this type is a polypeptide having the amino acid sequence H-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-$NH_2$ (SEQ ID NO:3). Zero, one, two or three amino acids in the thrombin peptide derivative differ from the amino acid at the corresponding position of SEQ ID NO:6, 1, 2, or 3. Preferably, the difference is conservative as for conservative substitutions of the thrombin peptide derivatives.

One example of a thrombin peptide derivative dimer provided herein is represented by Formula (IV) (core sequences disclosed as SEQ ID NO: 3):

In a specific embodiment, each polypeptide in the dimer is from 12 to 23 amino acid residues in length and independently includes Asp-Ala-Cys-$X_1$-Gly-Asp-Ser-Gly-Gly-Pro-$X_2$-Val (SEQ ID NO:10), wherein $X_1$ is Glu or Gln and $X_2$ is Phe, Met, Leu, His or Val, where each polypeptide optionally has a C-terminal amide, and where each polypeptide optionally has an acylated N-terminus. In another specific embodiment, each thrombin peptide derivative including a dimer includes a polypeptide including the amino acid sequence SEQ ID NO:27: Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-Met-Lys-Ser-Pro-Phe-Asn-Asn-Arg-Trp-Tyr, or a C-terminal truncated fragment thereof having at least twenty-three amino acids. More preferably, each thrombin peptide derivative includes the amino acid sequence SEQ ID NO:28: Ala-Gly-Tyr-Lys-Pro-Asp-Glu-Gly-Lys-Arg-Gly-Asp-Ala-Cys-$X_1$-Gly-Asp-Ser-Gly-Gly-Pro-$X_2$-Val-Met-Lys-Ser-Pro-Phe-Asn-Asn-Arg-Trp-Tyr, or a C-terminal truncated fragment thereof including at least twenty-three amino acids. $X_1$ is Glu or Gln and $X_2$ is Phe, Met, Leu, His or Val. Preferably $X_1$ is Glu, and $X_2$ is Phe. One example of a thrombin peptide derivative of this type is a polypeptide including the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-Met-Lys-Ser-Pro-Phe-Asn-Asn-Arg-Trp-Tyr (SEQ ID NO:27). A further example of a thrombin peptide derivative of this type is a polypeptide including the amino acid sequence H-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-Met-Lys-Ser-Pro-Phe-Asn-Asn-Arg-Trp-Tyr-$NH_2$ (SEQ ID NO:29). Zero, one, two or three amino acids in the thrombin peptide derivative differ from the amino acid at the corresponding position of SEQ ID NO:27, 28 or 29. Preferably, the difference is conservative as defined for conservative substitutions of the thrombin peptide derivatives.

Compositions

A thrombin peptide derivative useful in the methods described herein may be present in a composition. In one embodiment, a composition includes a pharmaceutically acceptable carrier. As used herein "pharmaceutically acceptable carrier" includes, but is not limited to, saline, solvents, dispersion media, coatings, antibacterial and antifungal agents, isotonic and absorption delaying agents, and the like, compatible with pharmaceutical administration. Additional active compounds can also be incorporated into a composition.

Suitable pharmaceutically acceptable carriers may contain inert ingredients which do not interact with the thrombin peptide derivative. A pharmaceutically acceptable carrier

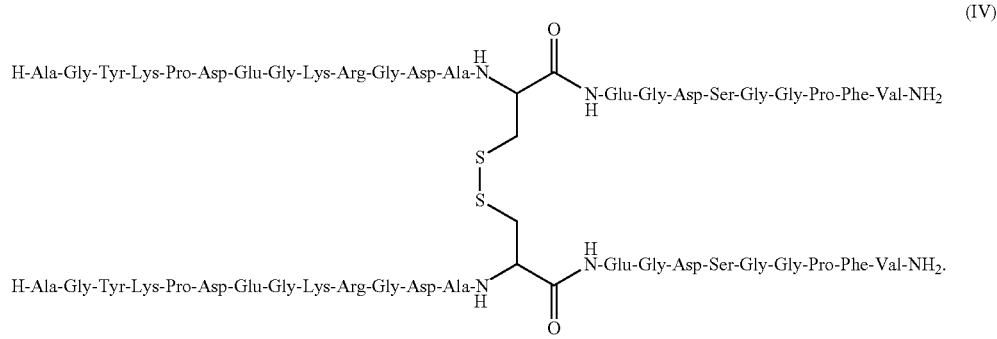

(IV)

should be biocompatible, i.e., non-toxic, non-inflammatory, non-immunogenic and devoid of other undesired reactions at the administration site. Examples of pharmaceutically acceptable carriers include, for example, saline, aerosols, commercially available inert gels, or liquids supplemented with albumin, methyl cellulose or a collagen matrix. Standard pharmaceutical formulation techniques can be employed, such as those described in Remington's Pharmaceutical Sciences, Mack Publishing Company, Easton, Pa.

The compositions used in the methods provided herein can additionally include a pharmaceutically acceptable carrier in which the thrombin peptide derivative is dissolved or suspended. Examples of pharmaceutically acceptable carriers include, for example, saline, aerosols, commercially available inert gels, or liquids supplemented with albumin, methyl cellulose or a collagen matrix.

A composition may be prepared by methods well known in the art of pharmaceutics. In general, a composition can be formulated to be compatible with its intended route of administration. Administration may be systemic or local. In some aspects local administration may have advantages for site-specific, targeted disease management. Local therapies may provide high, clinically effective concentrations directly to the treatment site, with less likelihood of causing systemic side effects. Examples of dosage forms are those suitable for oral, mucosal (e.g., nasal, sublingual, vaginal, buccal, or rectal), parenteral (e.g., subcutaneous, intravenous, bolus injection, intramuscular, or intraaterial), or transdermal administration.

Injectable delivery formulations may be administered intravenously or directly at the site in need of treatment. The injectable carrier may be a saline, a viscous solution, or a gel.

Ointments are typically prepared using an oleaginous base, e.g., containing fixed oils or hydrocarbons, such as white petrolatum or mineral oil, or an absorbent base, e.g., consisting of an absorbent anhydrous substance or substances, for example anhydrous lanolin. Following formation of the base, the active ingredients are added in the desired concentration.

Creams generally include an oil phase (internal phase) containing typically fixed oils, hydrocarbons, and the like, such as waxes, petrolatum, mineral oil, and the like, and an aqueous phase (continuous phase), including water and any water-soluble substances, such as added salts. The two phases are stabilized by use of an emulsifying agent, for example, a surface active agent, such as sodium lauryl sulfate; hydrophilic colloids, such as acacia colloidal clays, beegum, and the like. Upon formation of the emulsion, the active ingredients are added in the desired concentration.

Gels contain a base selected from an oleaginous base, water, or an emulsion-suspension base, as previously described. To the base is added a gelling agent which forms a matrix in the base, increasing its viscosity to a semisolid consistency. Examples of gelling agents are hydroxypropyl cellulose, acrylic acid polymers, and the like. The active ingredients are added to the formulation at the desired concentration at a point preceding addition of the gelling agent.

Delivery formulations include physiological saline, bacteriostatic saline (saline containing about 0.9% mg/mL benzyl alcohol), phosphate-buffered saline, Hank's solution, Ringer's-lactate, or liquids supplemented with albumin, methyl cellulose, or hyaluronic acid. Injectable matrices include polymers of poly(ethylene oxide) and copolymers of ethylene and propylene oxide (see Cao et al, *J. Biomater. Sci* 9:475 (1998) and Sims et al, *Plast Reconstr. Surg.* 98:843 (1996)).

Methods for encapsulating compositions (such as in a coating of hard gelatin or cyclodextran) are known in the art (Baker, et al, "Controlled Release of Biologically Active Agents", John Wiley and Sons, 1987).

In an embodiment, a thrombin peptide derivative is administered systemically. As used herein, "systemic administration" is understood as various routes of administration wherein the agent is delivered to the subject in a manner that the agent is distributed throughout the body, and is administered at a location remote from the specific site of action of the agent. As used herein, systemic administration includes, for example, non-topical, parenteral routes of administration. For example, systemic administration as used herein includes administration by injection, e.g., intravenously, subcutaneously, intramuscularly, transcutaneously, intradermally, intraperitoneally, intracranially; infusion, mucosally, and intranasally. In one embodiment, the thrombin peptide derivative is administered by injection. Examples of injection include infusion and intracranial injection, such as injection directly into a medulloblastoma.

The present invention is illustrated by the following examples. It is to be understood that the particular examples, materials, amounts, and procedures are to be interpreted broadly in accordance with the scope and spirit of the invention as set forth herein.

EXAMPLE 1

Materials and Methods

Reagents Used.

Human medulloblastoma Daoy cells (ATCC® HTB-186™) and human primary glioblastoma U87-MG cells (ATCC® HTB-14™) were purchased from American Tissue Culture Collection (ATCC) (Manassas, Va.) were maintained in EMEM medium as per the manufacturer's recommendation. Both cells lines were authenticated by BioSynthesis DNA Identity Center in 2013. Antibodies used include: anti-CD44, ANTI-Sox-2 (Cell Signaling Technology, Danvers, Mass.); anti-proliferating cell nuclear antigen (PCNA), anti-DCAMKL1, and anti-GPCR GPR49 (LgrS) for Western Blot analysis (Abcam, Cambridge, Mass.); anti-LgrS/GPR49 for IF analysis (Abgent, San Diego, Calif.); anti-active caspase-3 and anti-CD133 (Millipore, Temecula, Calif.); anti-β-actin (total) (Sigma, St Louis, Mo.). Alexa Fluor-594 and Alexa Fluor-488 coupled secondary IgG were from Invitrogen (Carlsbad, Calif.). TP508 was synthesized by American peptide as a lyophilized powder; a new batch of TP508 was prepared fresh in the lab for each experiment by dissolving the peptide in sterile saline.

In vitro growth of cells as primary and secondary 3D spheroids.

Brain cancer cells were grown as spheroids in vitro, as described by Kantara et. al., 2014, Cancer Res., 74:2487. Briefly, cells were plated at a density of 15000-30000 cells/well into 24-well ultra-low-attachment plates (Costar, Corning N.Y.), in serum-free media containing DMEM/F12 (1:1)+1% Antibiotic-Antimycotic (100×) supplemented with B-27 (50×) (Invitrogen), epidermal growth factor (EGF) 20 ng/ml and fibroblast growth factor (bFGF) (10 ng/ml) (Sigma-Aldrich, St Louis, Mo.). Media was changed every 2-3 days and the formation of spheroids monitored daily. Spheroids were imaged with an inverted microscope, at 4×, 10× and 40× using white light microscopy (Nikon Eclipse TS100, Melville, N.Y.). In initial experiments, cells were plated at increasing numbers to optimize the spheroid assay. Based on the results, an optimal number of 15000 cells were chosen for growing primary spheroids from brain cancer cells. For generating secondary spheroids, wells containing primary spheroids were enzymatically dissociated into single cells and cells from the primary wells, containing either Saline or TP508 were re-plated in low-attachment plates as secondary spheres.

Treatment of Brain Cancer Neurospheres/Spheroids In Vitro.

Primary spheroids were grown as described above. On Day 3, primary spheroids started forming and by day 5 after seeding the cells, spheroids were well-formed and ready for treatment. Spheroids were treated with optimally effective concentrations of TP508 (1 mg/mL). On day 7, 48 hrs post-treatment, spheroids were irradiated at 10Gy using a $Cs^{137}$ source. One nanodot purchased from LANDAUER was placed on top of the 24 well plates to confirm the actual amount of radiation delivered to the spheroids. On day 8, 24 hrs post-radiation, primary spheroids were enzymatically dissociated, and cells were re-plated in low-attachment plates. Secondary spheroids began to grow by day 10. A schematic depicting the steps of the procedure is shown in FIG. 1.

For the Relapse Experiment.

Control (Saline) and treated (TP508) primary-spheroids, were dissociated and re-plated as secondary-spheroids. Images were taken daily with white light microscopy to examine regrowth potential of the cells in each group. Formation of secondary spheroids was counted daily in each well and both control/treated secondary spheroids were also processed for western blotting (WB) analysis.

Western blot (WB) analysis of cells growing as 3D-spheroids.

Cells growing as 3D-spheroids were harvested and processed for preparing cellular lysates, followed by electrophoresis and transfer to PVDF-membranes as described in Kantara et. al., 2014, Cancer Res., 74:2487. Blots were cut into horizontal strips containing target or loading control proteins, and processed for detection of antigen-antibody complexes by chemiluminescese. Antigen-antibody complexes were detected with chemiluminescent reagent kit (GE Health Care). Membrane-strips containing either target or loading control proteins were simultaneously exposed to autoradiographic films whenever possible. In cases where limited samples were analyzed for multiple target proteins, the loading control β-actin was measured in a corresponding sample containing equivalent protein. In a few cases, the β-actin was stripped to measure target protein with similar molecular mass within the same membrane. Relative band density on scanned autoradiograms was analyzed using Image J program (rsbweb.nih.gov/ij/download), and expressed as a ratio of β-actin in the corresponding samples.

Cell Viability/Proliferation/Apoptosis.

Spheroids were enzymatically dissociated and measured by trypan blue exclusion test as described in Kantara et. al 2014. Dye exclusion was used as a measure of cell viability using Cellometer™ Auto T4 (Nexcelom Bioscience, Lawrence, Mass.). For assessing % cells undergoing apoptosis and proliferation, control and treated spheroids were dissociated enzymatically, cytospun onto slides, fixed and processed for immunofluorescent staining with antibodies against apoptotic-marker (activated-caspase-3) and proliferation-marker (PCNA).

Immunofluorescent Staining of Dissociated Spheroids.

Dissociated cells from secondary spheroids were cytospun on glass cover slips and processed for IF staining as described in Kantara et. al., 2014, Cancer Res., 74:2487. Cells were fixed using a 1:1 ratio of acetone:methanol solution at −20° C. for 20 min. Cells were then washed 3× with 1×PBS, and blocked with 5% goat serum for 1 h. Cells were then stained with either anti-CD133-antibody (1:100), anti-Sox-2-antibody (1:100), or anti-LgrS-antibody (1:100). Excess antibody was washed off, and cells were incubated with either goat anti-rabbit-IgG coupled to Alexa Fluor 488 (for detecting CD44 and LgrS) or goat anti-mouse-IgG coupled to Alexa Fluor 594 (for detecting CD133 and Sox-2). Excess antibody was washed off and cells were incubated with 4',6-diamidino-2-phenylindole (DAPI) for 2 minutes. Cover slips were then mounted onto glass slides using FluorSave™ Reagent (CALBIOCHEM, La Jolla, Calif.), and images acquired using Zeiss Axioplan epifluorencent microscope.

Paraffin embedding processing and immunofluorescent staining of intact primary spheroids.

Medulloblastoma Daoy primary spheroids growing in low-attachment plates were treated with RT±TP508 as described in method section. At about 4 days post-radiation, intact spheroids were gently collected, washed with PBS and fixed for 4 hrs with 10% formalin. Next, spheroids were resuspended in 2% agar gel containing 0.05% sodium azide and agar gel was allowed to solidify at 4° C. for 1 hr. Spheroids were then paraffin embedded, sectioned (5 µm) and stained by immunofluorescense (as described in Kantara et. al., 2014, Cancer Res., 74:2487) for specific cancer stem cell markers CD133, CD44, LGR5, pluripotent factor Sox-2, proliferative marker PCNA and apoptotic marker Activated Caspase-3.

In Vivo Growth of Tumor Xenografts in Athymic Nude Mice.

Daoy medulloblastoma cells were grown as 2D monolayers in T-75 flasks. At 60% confluency, cells were treated once with either Saline or TP508 (0.5 mg/mL) followed 48 hrs later by irradiation (0Gy or 10Gy). At 24 h post-radiation, cells were collected, washed and resuspended in PBS as single cell suspension. 1×10^6 cells/100 µL PBS were inoculated on both the right and left flanks of 6 week old male athymic nude mice (Taconic Farms) to allow for the growth of subcutaneous xenografts. Tumors were allowed to grow for 9 weeks. Mice were divided into 4 groups (n=2/group): 0Gy+Saline, 0Gy+TP508, 10Gy+Saline and 10Gy+TP508. Tumor volume was measured weekly in millimeters using the following formula: $(L \times W^2)/2$ where L=length and W=width. Mice were sacrificed at 9 weeks post-implant, tumors were removed and weighed. Data is presented as a line graph and table format, additionally tumor volume data from all 4 groups are presented as bar graphs as shown below.

Statistical Analysis of Data.

Data are presented as mean±SEM of values obtained from 4-6 samples/experiment from 8 total experiments. To test for significant differences between means, nonparametric Mann-Whitney test and T-Test was employed using GraphPad Prism software, Inc (La Jolla, Calif.); P values were considered statistically significant if less than 0.05.

Results

In vitro Studies

TP508 Decreases Cell Viability, Tumor Heterogeneity and Relapse Potential of Medulloblastoma Cancer Cells In Vitro, Post-RT.

Figure 2A:
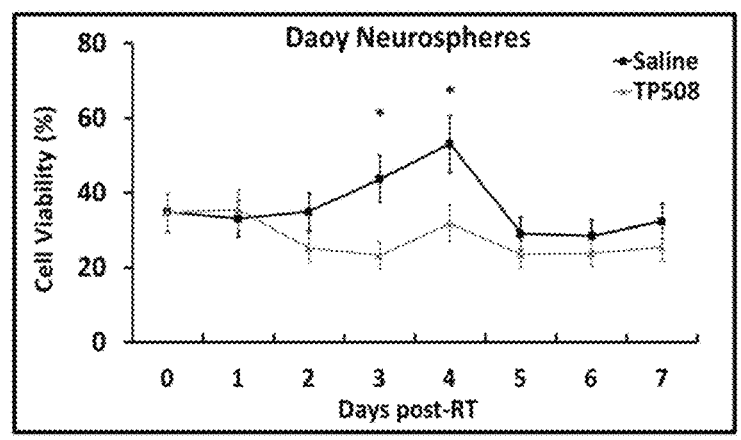
FIG. 2A, Cell viability of cancer stem cells treated with RT±TP508.
Figure 2B:
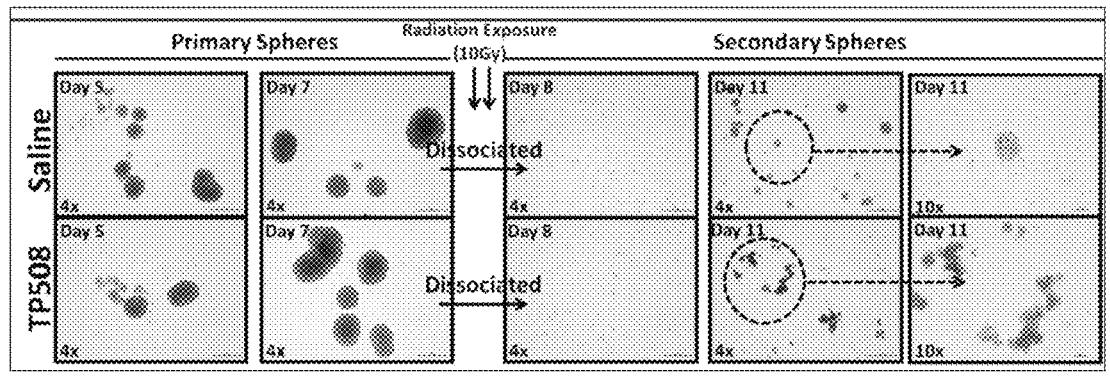
FIG. 2Bi, Formation of secondary spheroids when treated with RT±TP508.
Figure 2D:
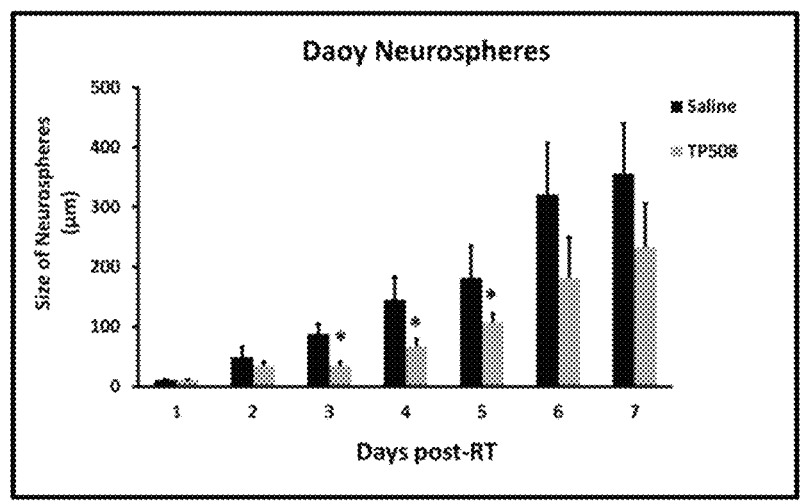
FIG. 2D, Size of secondary neurospheres treated with RT±TP508.

Medulloblastoma Daoy cells were grown and treated as described in the Method section. On day 8, primary spheroids were dissociated and re-plated to assess secondary spheroid formation. The number of secondary spheroids indicates the relapse potential of cancer stem cells while the size of the secondary spheroids indicates heterogeneity of the cell population. Results showed that TP508 decreases the viability of cancer stem cells compared to the control group (FIG. 2A). Additionally, a single treatment of TP508 48 hrs prior to radiation delayed the relapse potential of secondary spheroids by 1-2 days (bottom row) compared to the control (top row) (FIG. 2B). As can be seen in FIG. 2Bi, secondary spheroids in the saline treated group started forming by day 2-3 whereas secondary spheroids in the TP508 treated group started forming by days 3-4. Interestingly, primary spheres treated with TP508 fail to form well rounded spheroids and instead form small aggregates indicative of loss of stemness potential FIG. 2Bii. Furthermore, treating primary spheroids with TP508 48 hrs pre-radiation resulted in a significant decrease in the number and size of secondary spheroids formed post-RT compared to the saline treated group as shown in FIG. 2C and FIG. 2D, respectively. TP508 decreased cell viability, heterogeneity, stemness and relapse potential of cancer stem cells, suggesting that TP508 sensitizes cancer stem cells to radiation therapy, making these cells more susceptible.

TP508 Decreases the Expression and Proliferation of Cancer Stem Cells while Increasing Apoptosis.

Figure 3A:
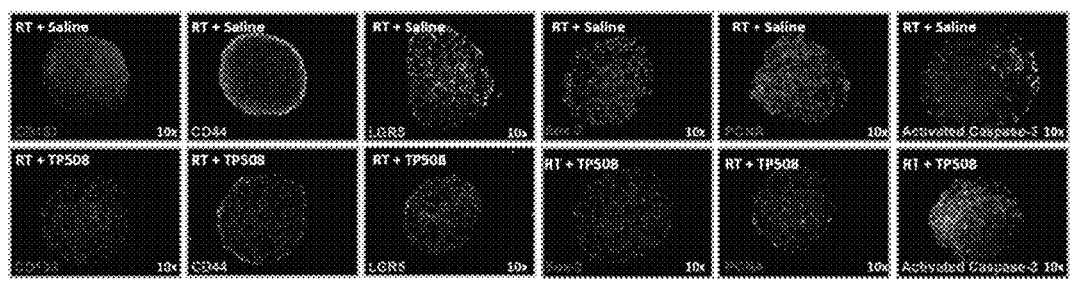
FIG. 3A, TP508 decreases the stemness potential of medulloblastoma cancer stem cells post-radiation exposure.
Figure 3B:
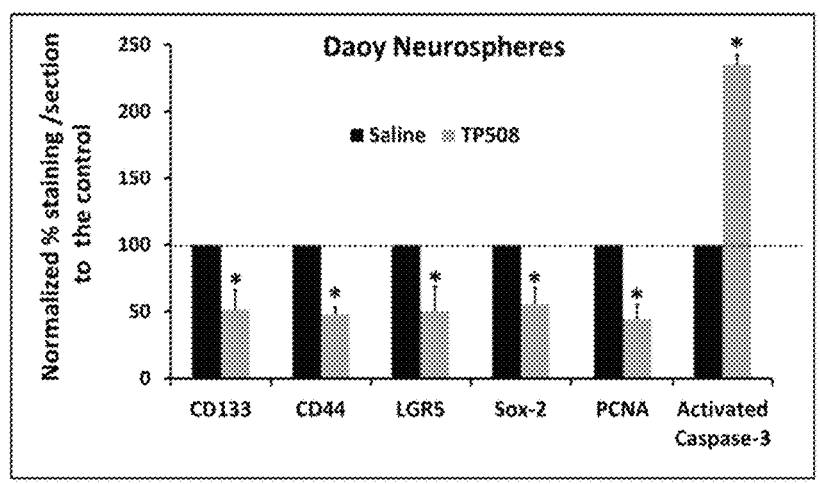
FIG. 3B, Quantitative analysis of cancer stem cell expression, proliferation and apoptosis post-RT+Saline vs RT+TP508 treatments.
Figure 3C:
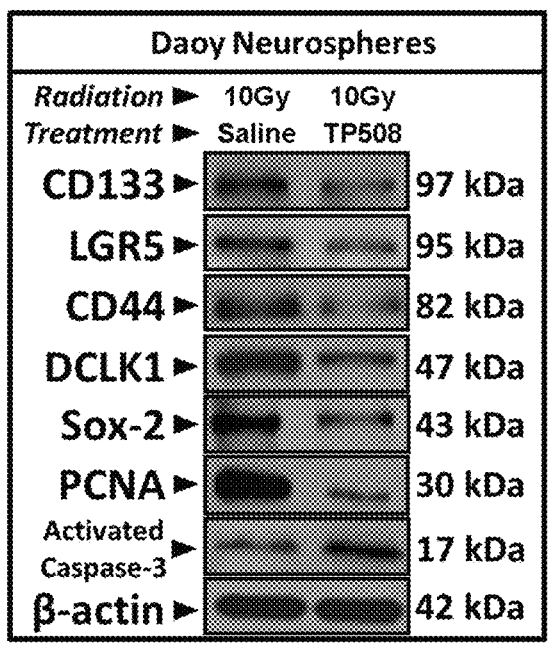
FIG. 3C, Western blot analysis of cancer stem cells treated with RT±TP508.
Figure 3D:
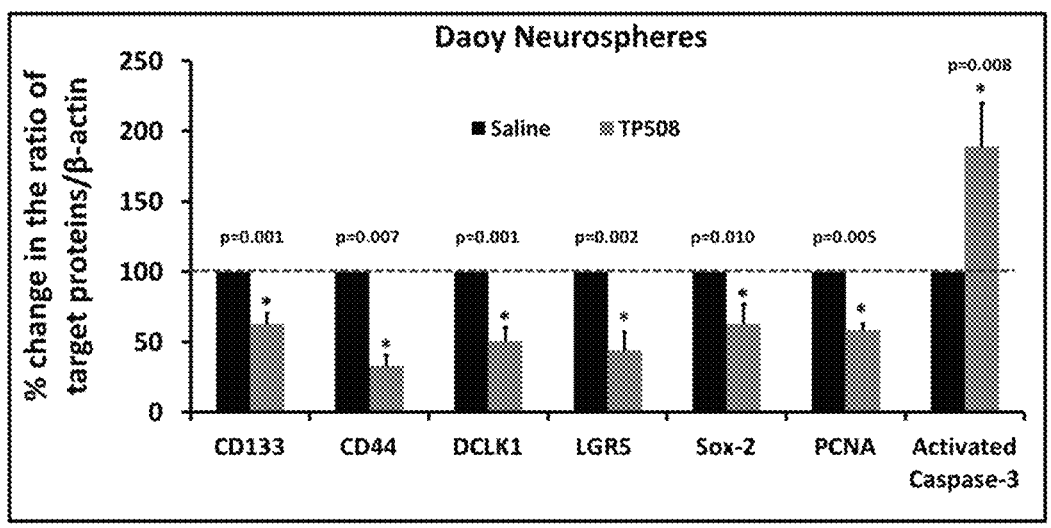
FIG. 3D, Percent change in the expression of the indicated markers in RT±TP508 treated groups.

Medulloblastoma Daoy primary spheroids (neurospheres) treated with RT±TP508 were stained by immunofluorescence 4 days post-radiation. Results show that expression of cancer stem cell markers CD133, CD44, LGR5 and pluripotent factor Sox-2 are significantly decreased in the RT+TP508 group compared to the control RT+Saline (FIG. 3A). Furthermore, proliferation (PCNA) of cancer stem cells is decreased in the RT+TP508 compared to the RT+Saline group, while apoptosis (activated caspase-3) is increased. More specifically, TP508 decreases the stemness and proliferative potential of medulloblastoma cancer stem cells by ~50% and increases apoptosis by ~65% compared to the control (FIG. 3B). Western Blot analysis of cancer stem cells treated with RT±TP508 was also performed as described in the Method section. Results show that TP508 significantly decreases the expression of cancer stem cell markers CD44, CD133, LRG5 and proliferation (PCNA) while increasing apoptosis (activated caspase-3) (FIG. 3C). Bar graph illustrating the percent change in the expression of the indicated markers compared to the control group is presented in FIG. 3D. These finding suggest that TP508 may be sensitizing cancer stem cells to radiation and making them more susceptible to radiation exposure. A decrease in these stem cell markers is also indicative of a less tumorigenic population of cells, hence Daoy cancer cells seems to become less malignant.

In Vivo Studies:

TP508 Inhibits the Growth of Daoy Medulloblastoma Tumor Xenografts In Vivo.

Figure 4A:
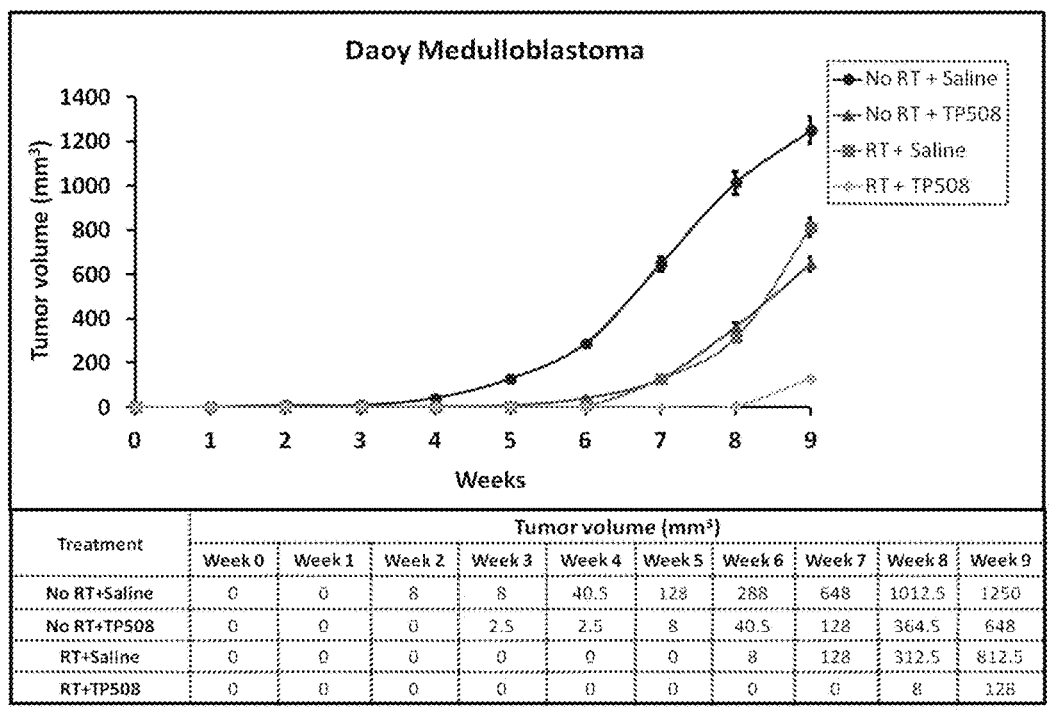
FIG. 4A, Tumor volumes measured at the specific time points.
Figure 4B:
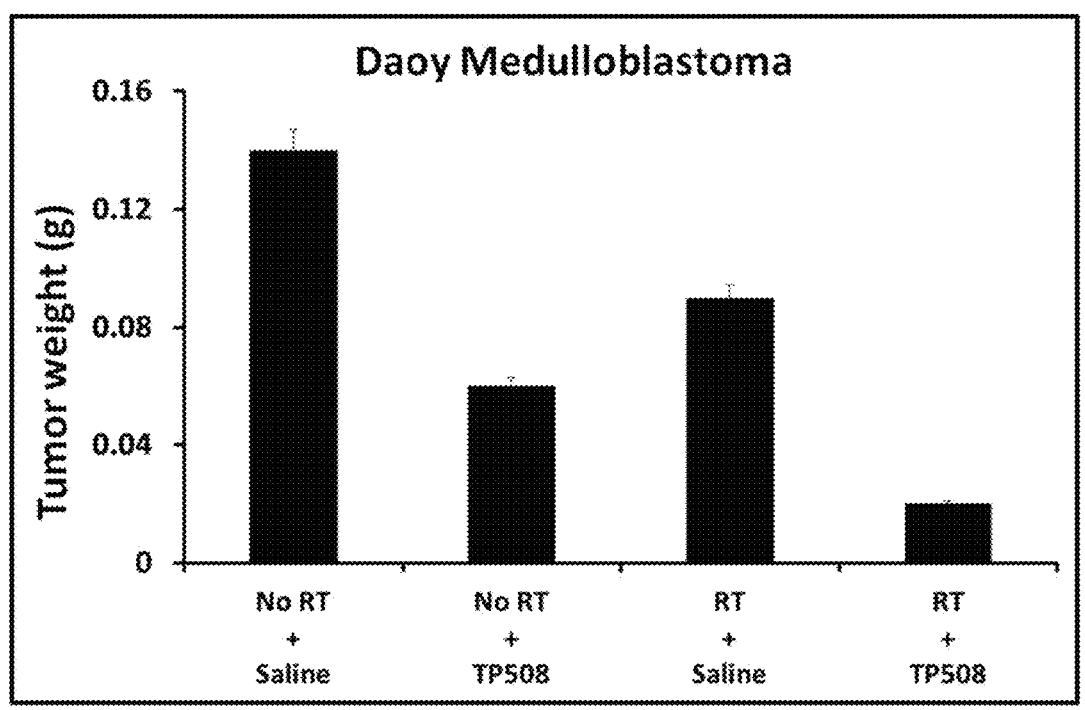
FIG. 4B, Tumor weights at time of sacrifice.

Athymic nude mice were inoculated subcutaneously with 1×10^6 Daoy cells pre-treated with ±RT±TP508. By week 9, tumors notably varied in size between all four groups in the order of No RT+Saline>RT+Saline>No RT+TP508>RT+TP508 (FIG. 4A). At 9 weeks post-implant, mice were euthanized and tumors were weighed. Tumor weights between groups positively correlated with tumor volumes (FIG. 4B). Results show that non-irradiated saline treated Daoy cells are able to form large tumors as illustrated by the line "No RT+Saline" in FIG. 4A. However, when non-irradiated cells are pre-treated with TP508, these cells grow smaller tumor xenografts, as illustrated by the line "No RT+TP508" in FIG. 4A. Tumor growth is approximately decreased by 50% compared to the No RT+Saline group. Upon radiation and saline pre-treatment (line "RT+Saline"), tumor growth is inhibited by ~30% compared to the No RT+Saline group. Interestingly, when Daoy cells are irradiated and treated with TP508 (line "RT+TP508"), tumor growth is significantly inhibited and is decreased by >75% compared to the RT+Saline group and >90% compared to the No RT+saline group. Results of tumor weights demonstrate a similar trend as tumor volume and confirm that RT+TP508 treatment of Doay cells significantly decreases tumor growth compared to only radiation or TP508 treatment. Our results suggest that radiation treatment alone or TP508 treatment alone of Daoy cells significantly decreases tumor growth of medulloblastoma cells; however combined treatment of radiation and TP508 seems to be most effective in preventing their tumor growth.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method comprising:
   administering to a subject having a medulloblastoma an effective amount of a thrombin peptide derivative, wherein the thrombin peptide derivative comprises Asp-Ala-R, wherein R is a serine esterase conserved sequence, and wherein the serine esterase conserved sequence comprises the sequence Cys-$X_1$-Gly-Asp-Ser-Gly-Gly-Pro-$X_2$-Val (SEQ ID NO:15), wherein $X_1$ is Glu or Gln and $X_2$ is Phe, Met, Leu, His or Val; and
   exposing cells of the medulloblastoma of the subject to a therapeutic radiation,
   wherein the thrombin peptide derivative is administered before the therapeutic radiation,
   wherein the thrombin peptide derivative is administered between 1 hour and 60 hours before the exposing;
   and wherein viability of cells of the medulloblastoma is decreased compared to viability of cells of the medulloblastoma before the administering and the exposing.

2. The method of claim 1 wherein the cells of the medulloblastoma having decreased viability comprise cancer stem cells.

3. The method of claim 1 wherein the administration is systemic.

4. The method of claim 3 wherein the systemic administration is intravenous.

5. The method of claim 1 wherein the subject is a child or young adult.

6. The method of claim 1 wherein the medulloblastoma is a relapse following an initial treatment.

7. The method of claim 1 wherein the thrombin peptide derivative comprises the sequence Arg-Gly-Asp-Ala-Cys-$X_1$-Gly-Asp-Ser-Gly-Gly-Pro-$X_2$-Val (SEQ ID NO:1), wherein $X_1$ is Glu or Gln and $X_2$ is Phe, Met, Leu, His or Val.

8. The method of claim 1 wherein the thrombin peptide derivative comprises the sequence Ala-Gly-Tyr-Lys-Pro-Asp-Glu-Gly-Lys-Arg-Gly-Asp-Ala-Cys-$X_1$-Gly-Asp-Ser-Gly-Gly-Pro-$X_2$-Val (SEQ ID NO:2), an N-terminal truncated fragment thereof comprising at least fourteen amino acid residues, wherein $X_1$ is Glu or Gln and $X_2$ is Phe, Met, Leu, His or Val.

9. The method of claim 1 wherein the thrombin peptide derivative is H-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-$NH_2$ (SEQ ID NO:3).

10. A method of comprising:
    administering to a subject having a medulloblastoma an effective amount of a thrombin peptide derivative, wherein the thrombin peptide derivative comprises the polypeptide Arg-Gly-Asp-Ala-Xaa-$X_1$-Gly-Asp-Ser-Gly-Gly-Pro-$X_2$-Val (SEQ ID NO:4), wherein Xaa is alanine, glycine, serine or an S-protected cysteine; $X_1$ is Glu or Gln; and $X_2$ is Phe, Met, Leu, His or Val; and
    exposing cells of the medulloblastoma of the subject to a therapeutic radiation, wherein the thrombin peptide derivative is administered before the therapeutic radiation, wherein the thrombin peptide derivative is administered between 1 hour and 60 hours before the exposing;

and wherein viability of cells of the medulloblastoma is decreased compared to viability of cells of the medulloblastoma before the administering and the exposing.

11. The method of claim 1 wherein the thrombin derivative comprises a C-terminal amide, an acylated N-terminus, or a combination thereof, wherein said C-terminal amide is represented by —C(O)NR$_a$R$_b$, wherein R$_a$ and R$_b$ are independently hydrogen, an aliphatic group comprising up to 10 carbon atoms, or R$_a$ and R$_b$, taken together with the nitrogen to which they are bonded, form a C$_3$-C$_{10}$ non-aromatic heterocyclic group, and wherein said N-terminal acyl group is represented by R$_c$C(O)—, where R$_c$ is hydrogen, an aliphatic group comprising up to 10 carbon atoms or a phenyl group optionally substituted with one or more groups selected from C$_1$-C$_6$ alkyl, C$_1$-C$_6$ alkoxy, C$_1$-C$_6$ haloalkyl, C$_1$-C$_6$ haloalkoxy, nitro and cyano.

12. A method comprising:
administering to a subject having a medulloblastoma an effective amount of a thrombin peptide derivative, wherein the thrombin peptide derivative comprises Asp-Ala-R, wherein R is a serine esterase conserved sequence, and wherein the serine esterase conserved sequence comprises the sequence Cys-X$_1$-Gly-Asp-Ser-Gly-Gly-Pro-X$_2$-Val (SEQ ID NO:15), wherein X$_1$ is Glu or Gln and X$_2$ is Phe, Met, Leu, His or Val; and
exposing cells of the medulloblastoma of the subject to a therapeutic radiation,
wherein the thrombin peptide derivative is administered before the therapeutic radiation,
wherein the thrombin peptide derivative is administered between 1 hour and 60 hours before the exposing;
and wherein shrinkage of the medulloblastoma in the subject is increased compared to shrinkage of the medulloblastoma before the administrating and the exposing.

13. The method of claim 12 wherein the administration is systemic.

14. The method of claim 13 wherein the systemic administration is intravenous.

15. The method of claim 12 wherein the subject is a child or young adult.

16. The method of claim 12 wherein the medulloblastoma is a relapse following an initial treatment.

17. The method of claim 12 wherein the thrombin peptide derivative comprises the sequence Arg-Gly-Asp-Ala-Cys-X$_1$-Gly-Asp-Ser-Gly-Gly-Pro-X$_2$-Val (SEQ ID NO:1), wherein X$_1$ is Glu or Gln and X$_2$ is Phe, Met, Leu, His or Val.

18. The method of claim 12 wherein the thrombin peptide derivative comprises the sequence Ala-Gly-Tyr-Lys-Pro-Asp-Glu-Gly-Lys-Arg-Gly-Asp-Ala-Cys-X$_1$-Gly-Asp-Ser-Gly-Gly-Pro-X$_2$-Val (SEQ ID NO:2), an N-terminal truncated fragment thereof comprising at least fourteen amino acid residues, wherein X$_1$ is Glu or Gln and X$_2$ is Phe, Met, Leu, His or Val.

19. The method of claim 12 wherein the thrombin peptide derivative is H-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-NH$_2$ (SEQ ID NO:3).

20. A method comprising:
administering to a subject having a medulloblastoma an effective amount of a thrombin peptide derivative, wherein the thrombin peptide derivative comprises the polypeptide Arg-Gly-Asp-Ala-Xaa-X$_1$-Gly-Asp-Ser-Gly-Gly-Pro-X$_2$-Val (SEQ ID NO:4), wherein Xaa is alanine, glycine, serine or an S-protected cysteine; X$_1$ is Glu or Gln; and X$_2$ is Phe, Met, Leu, His or Val; and
exposing cells of the medulloblastoma of the subject to a therapeutic radiation,
wherein the thrombin peptide derivative is administered before the therapeutic radiation
wherein the thrombin peptide derivative is administered between 1 hour and 60 hours before the exposing;
and wherein shrinkage of the medulloblastoma in the subject is increased compared to shrinkage of the medulloblastoma before the administrating and the exposing.

21. The method of claim 12 wherein the thrombin derivative comprises a C-terminal amide, an acylated N-terminus, or a combination thereof, wherein said C-terminal amide is represented by —C(O)NR$_a$R$_b$, wherein R$_a$ and R$_b$ are independently hydrogen, an aliphatic group comprising up to 10 carbon atoms, or R$_a$ and R$_b$, taken together with the nitrogen to which they are bonded, form a C$_3$-C$_{10}$ non-aromatic heterocyclic group, and wherein said N-terminal acyl group is represented by R$_c$C(O)—, where R$_c$ is hydrogen, an aliphatic group comprising up to 10 carbon atoms or a phenyl group optionally substituted with one or more groups selected from C$_1$-C$_6$ alkyl, C$_1$-C$_6$ alkoxy, C$_1$-C$_6$ haloalkyl, C$_1$-C$_6$ haloalkoxy, nitro and cyano.

22. A method comprising:
contacting a medulloblastoma cancer cell with an effective amount of a thrombin peptide derivative, wherein the thrombin peptide derivative comprises Asp-Ala-R, wherein R is a serine esterase conserved sequence, and wherein the serine esterase conserved sequence comprises the sequence Cys-X$_1$-Gly- Asp-Ser-Gly-Gly-Pro-X$_2$-Val (SEQ ID NO:15), wherein X$_1$ is Glu or Gln and X$_2$ is Phe, Met, Leu, His or Val; and
exposing the medulloblastoma cancer cell to a therapeutic radiation,
wherein the medulloblastoma cancer cell is contacted with the thrombin peptide derivative before the radiation,
wherein the thrombin peptide derivative is administered between 1 hour and 60 hours before the exposing;
and wherein the viability of the medulloblastoma cancer cell is decreased compared to the viability of the medulloblastoma cancer before the contacting and exposing.

23. The method of claim 22 wherein the medulloblastoma cancer cell is ex vivo.

24. The method of claim 22 wherein the thrombin peptide derivative comprises the sequence Arg-Gly-Asp-Ala-Cys-X$_1$-Gly-Asp-Ser-Gly-Gly-Pro-X$_2$-Val (SEQ ID NO:1), wherein X$_1$ is Glu or Gln and X$_2$ is Phe, Met, Leu, His or Val.

25. The method of claim 22 wherein the thrombin peptide derivative comprises the sequence Ala-Gly-Tyr-Lys-Pro-Asp-Glu-Gly-Lys-Arg-Gly-Asp-Ala-Cys-X$_1$-Gly-Asp-Ser-Gly-Gly-Pro-$_2$-Val (SEQ ID NO:2), an N-terminal truncated fragment thereof comprising at least fourteen amino acid residues, wherein X$_1$ is Glu or Gln and X$_2$ is Phe, Met, Leu, His or Val.

26. The method of claim 22 wherein the thrombin peptide derivative is H-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-NH$_2$ (SEQ ID NO3).

27. A method comprising:
contacting a medulloblastoma cancer cell with an effective amount of a thrombin peptide derivative, wherein the thrombin peptide derivative comprises the polypeptide Arg-Gly-Asp-Ala-Xaa-X$_1$-Gly-Asp-Ser-Gly-Gly-Pro-X$_2$-Val (SEQ ID NO:4), wherein Xaa is alanine, glycine, serine or an S-protected cysteine; X$_1$ is Glu or Gln; and X$_2$ is Phe, Met, Leu, His or Val; and
exposing the medulloblastoma cancer cell to a therapeutic radiation,
wherein the medulloblastoma cancer cell is contacted with the thrombin peptide derivative before the radiation,
wherein the thrombin peptide derivative is administered between 1 hour and 60 hours before the exposing;
and wherein the viability of the medulloblastoma cancer cell is decreased compared to the viability of the medulloblastoma cancer before the contacting and exposing.

28. The method of claim 22 wherein the thrombin derivative comprises a C-terminal amide, an acylated N-terminus, or a combination thereof, wherein said C-terminal amide is represented by —C(O)NR$_a$R$_b$, wherein R$_a$ and R$_b$ are independently hydrogen, an aliphatic group comprising up to 10 carbon atoms, or R$_a$ and R$_b$, taken together with the nitrogen to which they are bonded, form a C$_3$-C$_{10}$ non-aromatic heterocyclic group, and wherein said N-terminal acyl group is represented by R$_c$C(O)—, where R$_c$ is hydrogen, an aliphatic group comprising up to 10 carbon atoms or a phenyl group optionally substituted with one or more groups selected from C$_1$-C$_6$ alkyl, C$_1$-C$_6$ alkoxy, C$_1$-C$_6$ haloalkyl, C$_1$-C$_6$ haloalkoxy, nitro and cyano.

29. The method of claim 10 wherein the cells of the medulloblastoma having decreased viability comprise cancer stem cells.

30. The method of claim 10 wherein the administration is systemic.

31. The method of claim 30 wherein the systemic administration is intravenous.

32. The method of claim 10 wherein the subject is a child or young adult.

33. The method of claim 10 wherein the medulloblastoma is a relapse following an initial treatment.

34. The method of claim 10 wherein the thrombin derivative comprises a C-terminal amide, an acylated N-terminus, or a combination thereof, wherein said C-terminal amide is represented by —C(O)NR$_a$R$_b$, wherein R$_a$ and R$_b$ are independently hydrogen, an aliphatic group comprising up to 10 carbon atoms, or R$_a$ and R$_b$, taken together with the nitrogen to which they are bonded, form a C$_3$-C$_{10}$ non-aromatic heterocyclic group, and wherein said N-terminal acyl group is represented by R$_c$C(O)—, where R$_c$ is hydrogen, an aliphatic group comprising up to 10 carbon atoms or a phenyl group optionally substituted with one or more groups selected from C$_1$-C$_6$ alkyl, C$_1$-C$_6$ alkoxy, C$_1$-C$_6$ haloalkyl, C$_1$-C$_6$ haloalkoxy, nitro and cyano.

35. The method of claim 20 wherein the administration is systemic.

36. The method of claim 35 wherein the systemic administration is intravenous.

37. The method of claim 20 wherein the subject is a child or young adult.

38. The method of claim 20 wherein the medulloblastoma is a relapse following an initial treatment.

39. The method of claim 20 wherein the thrombin derivative comprises a C-terminal amide, an acylated N-terminus, or a combination thereof, wherein said C-terminal amide is represented by —C(O)NR$_a$R$_b$, wherein R$_a$ and R$_b$ are independently hydrogen, an aliphatic group comprising up to 10 carbon atoms, or R$_a$ and R$_b$, taken together with the nitrogen to which they are bonded, form a C$_3$-C$_{10}$ non-aromatic heterocyclic group, and wherein said N-terminal acyl group is represented by R$_c$C(O)—, where R$_c$ is hydrogen, an aliphatic group comprising up to 10 carbon atoms or a phenyl group optionally substituted with one or more groups selected from C$_1$-C$_6$ alkyl, C$_1$-C$_6$ alkoxy, C$_1$-C$_6$ haloalkyl, C$_1$-C$_6$ haloalkoxy, nitro and cyano.

40. The method of claim 27 wherein the medulloblastoma cancer cell is ex vivo.

41. The method of claim 27 wherein the thrombin derivative comprises a C-terminal amide, an acylated N-terminus, or a combination thereof, wherein said C-terminal amide is represented by —C(O)NR$_a$R$_b$, wherein R$_a$ and R$_b$ are independently hydrogen, an aliphatic group comprising up to 10 carbon atoms, or R$_a$ and R$_b$, taken together with the nitrogen to which they are bonded, form a C$_3$-C$_{10}$ non-aromatic heterocyclic group, and wherein said N-terminal acyl group is represented by R$_c$C(O)—, where R$_c$ is hydrogen, an aliphatic group comprising up to 10 carbon atoms or a phenyl group optionally substituted with one or more groups selected from C$_1$-C$_6$ alkyl, C$_1$-C$_6$ alkoxy, C$_1$-C$_6$ haloalkyl, C$_1$-C$_6$ haloalkoxy, nitro and cyano.

* * * * *

UNITED STATES PATENT AND TRADEMARK OFFICE
CERTIFICATE OF CORRECTION

PATENT NO. : 10,220,078 B2  
APPLICATION NO. : 14/736735  
DATED : March 5, 2019  
INVENTOR(S) : Darrell Carney, Carla Kantara and Stephanie Moya It is certified that error appears in the above-identified patent and that said Letters Patent is hereby corrected as shown below:

In the Claims

In Claim 10, Column 36, Line 65, delete "X2" and replace with --$X_2$--

In Claim 25, Column 38, Line 64, delete "Gly-Gly-Pro-$_2$-Val" and replace with --Gly-Gly-Pro-$X_2$-Val--

Signed and Sealed this  
Thirtieth Day of July, 2019

Andrei Iancu  
*Director of the United States Patent and Trademark Office*